United States Patent
Tojo et al.

(10) Patent No.: US 9,315,727 B2
(45) Date of Patent: *Apr. 19, 2016

(54) COMPOUND HAVING FLUORINATED NAPHTHALENE STRUCTURE AND LIQUID CRYSTAL COMPOSITION OF THE SAME

(71) Applicant: DIC Corporation, Tokyo (JP)

(72) Inventors: Kenta Tojo, Kita-adachi-gun (JP); Tetsuo Kusumoto, Kita-adachi-gun (JP)

(73) Assignee: DIC CORPORATION (TOKYO), Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/428,196

(22) PCT Filed: Sep. 19, 2013

(86) PCT No.: PCT/JP2013/075266
§ 371 (c)(1),
(2) Date: Mar. 13, 2015

(87) PCT Pub. No.: WO2014/057780
PCT Pub. Date: Apr. 17, 2014

(65) Prior Publication Data
US 2015/0259599 A1    Sep. 17, 2015

(30) Foreign Application Priority Data
Oct. 9, 2012    (JP) .................. 2012-224114

(51) Int. Cl.
| C07C 41/00 | (2006.01) |
| C07C 43/00 | (2006.01) |
| C09K 19/00 | (2006.01) |
| C09K 19/30 | (2006.01) |
| C09K 19/32 | (2006.01) |
| C07C 43/225 | (2006.01) |
| C09K 19/04 | (2006.01) |
| C09K 19/34 | (2006.01) |

(52) U.S. Cl.
CPC ........... *C09K 19/3003* (2013.01); *C07C 43/225* (2013.01); *C09K 19/322* (2013.01); *C09K 2019/0448* (2013.01); *C09K 2019/0466* (2013.01); *C09K 2019/301* (2013.01); *C09K 2019/3422* (2013.01)

(58) Field of Classification Search
CPC .......... C07C 41/01; C07C 41/30; C09K 19/00
USPC ..................... 568/631, 634, 657; 252/299.61
See application file for complete search history.

(56) References Cited

U.S. PATENT DOCUMENTS

| 2005/0017216 A1 | 1/2005 | Poetsch et al. |
| 2006/0263542 A1 | 11/2006 | Kirsch et al. |
| 2007/0051919 A1 | 3/2007 | Kondou et al. |
| 2009/0065739 A1 | 3/2009 | Haseba et al. |
| 2010/0328600 A1 | 12/2010 | Shimada et al. |

FOREIGN PATENT DOCUMENTS

| JP | 2000-355560 A | 12/2000 |
| JP | 2001-019649 A | 1/2001 |
| JP | 2004-352721 A | 12/2004 |
| JP | 2007-070295 A | 3/2007 |
| JP | 2009-067780 A | 4/2009 |
| JP | 2013-170246 A | 9/2013 |
| KR | 10-2006-0119879 A | 11/2006 |
| WO | 2009/034867 A1 | 3/2009 |
| WO | 2013/018796 A1 | 2/2013 |
| WO | 2013/141116 A1 | 9/2013 |

OTHER PUBLICATIONS

International Search Report dated Dec. 10, 2013, issued in corresponding application No. PCT/JP2013/075266.
Written Opinion dated Dec. 10, 2013, issued in corresponding application No. PCT/JP2013/075266.

*Primary Examiner* — Sikarl Witherspoon
(74) *Attorney, Agent, or Firm* — Westerman, Hattori, Daniels & Adrian, LLP

(57) ABSTRACT

There is provided a liquid crystal composition containing the compound represented by the general formula (1) and a liquid crystal display device that uses the liquid crystal composition. The compound represented by the general formula (1) has high $\Delta\epsilon$, high $T_{ni}$, and good miscibility with other liquid crystal compounds. Therefore, a liquid crystal composition that has high $\Delta\epsilon$ and exhibits a liquid crystal phase in a wide temperature range can be obtained by using the compound represented by the general formula (1) as a component of the liquid crystal composition. Thus, the compound is very useful as a constituent component of the liquid crystal composition for liquid crystal display devices.

11 Claims, No Drawings

COMPOUND HAVING FLUORINATED NAPHTHALENE STRUCTURE AND LIQUID CRYSTAL COMPOSITION OF THE SAME

TECHNICAL FIELD

The present invention relates to a compound having a fluorinated naphthalene structure, which is useful for organic electronic materials, medicines and agricultural chemicals, and, in particular, materials for liquid crystal display devices.

BACKGROUND ART

Liquid crystal display devices have been used for clocks, calculators, measuring instruments, panels for automobiles, word processors, electronic organizers, printers, computers, televisions, clocks, advertising signage, etc. Typical examples of a liquid crystal display mode include a TN (twisted nematic) mode, an STN (super twisted nematic) mode, a vertical alignment mode that uses a TFT (thin film transistor), and an IPS (in-plane switching) mode. Liquid crystal compositions used for such liquid crystal display devices need to be stable against external factors such as moisture, air, heat, and light, exhibit a liquid crystal phase (e.g., nematic phase, smectic phase, and blue phase) in as wide as possible temperature range centered around room temperature, and have a low viscosity and a low drive voltage. Furthermore, such a liquid crystal composition needs to have optimum dielectric anisotropy ($\Delta\in$), optimum refractive index anisotropy ($\Delta n$), and the like for individual display devices.

In horizontal alignment displays with a TN mode, an STN mode, or an IPS mode, a liquid crystal composition whose $\Delta\in$ is positive has been used. Furthermore, a driving method has been reported in which a liquid crystal composition whose $\Delta\in$ is positive is vertically aligned when no voltage is applied and display is achieved by applying a horizontal electric field, and thus such a liquid crystal composition whose $\Delta\in$ is positive has been increasingly required. Therefore, components that constitute the liquid crystal composition need to have $\Delta\in$ as high as possible. When a liquid crystal composition is used in display devices or the like, the liquid crystal composition needs to exhibit a stable nematic phase in a wide temperature range. In order to maintain a nematic phase in a wide temperature range, individual components that constitute the liquid crystal composition need to have good miscibility with other components and a high clearing point ($T_{ni}$).

For the purpose of obtaining a compound having high $\Delta\in$, it is generally effective to intramolecularly introduce many fluorine atoms. For the purpose of obtaining a compound having high $T_{ni}$, it is effective to increase the number of ring structures contained in the molecule. However, compounds having a structure in which a plurality of ring structures are directly bonded to each other without including a linking group therebetween, that is, a so-called direct-ring structure, generally have high crystallinity. If a liquid crystal composition containing such a compound is cooled, crystals of the compound are precipitated. The precipitation of the compound from the liquid crystal composition changes the physical properties of the liquid crystal composition. Therefore, the compound added to the liquid crystal composition should not be separated or precipitated for a long time for practical reasons (storage stability).

For example, the following compound having a fluorinated naphthalene structure (refer to PTL 1) has a relatively high $\Delta\in$ and high $T_{ni}$.

[Chem. 1]

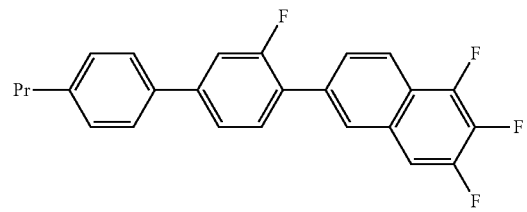

However, crystals may be precipitated by cooling depending on the components in the liquid crystal composition. Therefore, such a compound has poor storage stability.

The following compound having a —$CF_2O$— group introduced as a linking group has high $\Delta\in$ and good storage stability (refer to PTL 2). However, when the compound is added to a liquid crystal composition, $T_{ni}$ considerably decreases.

[Chem. 2]

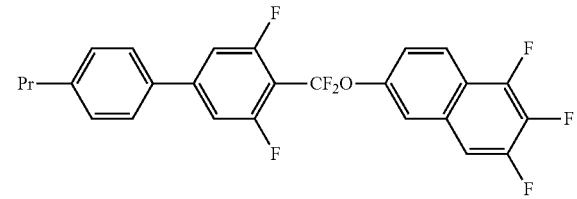

CITATION LIST

Patent Literature

PTL 1: Japanese Unexamined Patent Application Publication No. 2000-355560

PTL 2: Japanese Unexamined Patent Application Publication No. 2001-19649

SUMMARY OF INVENTION

Technical Problem

It is an object of the present invention to provide a compound having high $\Delta\in$, high $T_{ni}$, and good storage stability and also to provide a liquid crystal composition containing the compound as a constituent component and a liquid crystal display device.

Solution to Problem

To achieve the above object, the inventors of the present invention have studied various compounds, and consequently have completed the present invention.

The present invention provides a compound represented by general formula (1),

[Chem. 3]

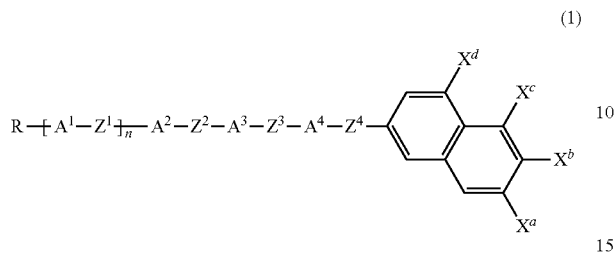

(1)

(in the formula, R represents an alkyl group having 1 to 15 carbon atoms or an alkenyl group having 2 to 15 carbon atoms; one —$CH_2$— or two or more non-adjacent —$CH_2$— in the groups may be each independently substituted with —O—, —S—, —COO—, —OCO—, or —CO—;
$A^1$ to $A^4$ are each independently selected from the group consisting of
(a) a 1,4-cyclohexylene group (one —$CH_2$— or two or more non-adjacent —$CH_2$— in this group may be each independently substituted with O— or —S—) and
(b) a 1,4-phenylene group (one —CH= or two or more non-adjacent —CH= in this group may be substituted with —N=, and a hydrogen atom in this group may be substituted with a fluorine atom or a chlorine atom);
$Z^1$ to $Z^4$ each independently represent —$CF_2O$—, —$OCF_2$—, —$CH_2CH_2$—, —$CF_2CF_2$—, —CH=CH—, —CF=CF—, —C≡C—, or a single bond, and at least one of $Z^1$ to $Z^4$ present in the compound represents —$CF_2O$— or —$OCF_2$—;
$X^a$ to $X^d$ each independently represent a hydrogen atom, a fluorine atom, or a chlorine atom; and n represents 0 or 1) and also provides a liquid crystal composition containing the compound and a liquid crystal display device that uses the liquid crystal composition.

Advantageous Effects of Invention

The compound represented by the general formula (1) and provided by the present invention has high Δ∈, high $T_{ni}$, and good miscibility with other liquid crystal compounds.

Accordingly, a liquid crystal composition that has high Δ∈ and exhibits a liquid crystal phase in a wide temperature range can be obtained by using the compound represented by the general formula (1) as a component of the liquid crystal composition. Thus, the compound is very useful as a constituent component of the liquid crystal composition for liquid crystal display devices.

DESCRIPTION OF EMBODIMENTS

In the general formula (1), for the purpose of decreasing the viscosity, R preferably represents an alkyl group having 1 to 8 carbon atoms or an alkenyl group having 2 to 8 carbon atoms, and particularly preferably represents an alkyl group having 1 to 5 carbon atoms or an alkenyl group having 2 to 5 carbon atoms. Furthermore, R preferably represents a linear group.

When an importance is given to a decrease in the viscosity, $A^1$ to $A^4$ present in the compound preferably each independently represent a trans-1,4-cyclohexylene group or an unsubstituted 1,4-phenylene group and more preferably each independently represent a trans-1,4-cyclohexylene group. When an importance is given to an increase in Δ∈, $A^1$ to $A^4$ preferably each independently represent one of the following structures.

[Chem. 4]

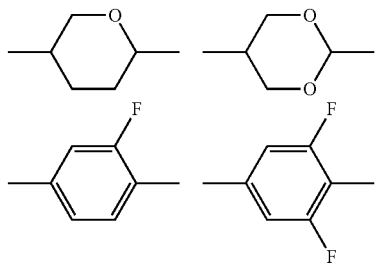

When an importance is given to the storage stability,

[Chem. 5]

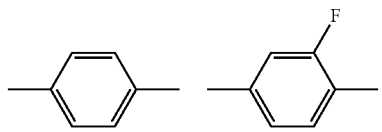

$A^1$ to $A^4$ preferably each independently represent one of the above structures.

When an importance is given to a decrease in the viscosity, $Z^1$ to $Z^3$ present in the compound preferably each independently represent —$CF_2O$—, —$OCF_2$—, —CF=CF—, or a single bond and more preferably each independently represent —$CF_2O$—, —$OCF_2$—, or a single bond.

When an importance is given to an increase in Δ∈, $Z^4$ preferably represents —$CF_2O$— or —$OCF_2$— and more preferably represents —$CF_2O$—.

When an importance is given to the balance among the viscosity, Δ∈, and the storage stability, $Z^1$ and $Z^2$ present in the compound preferably represent —$CH_2CH_2$— or a single bond.

Preferably, $Z^3$ represents —$CF_2O$— and $Z^4$ represents a single bond or $Z^3$ represents a single bond and $Z^4$ represents —$CF_2O$—.

When an importance is given to an increase in Δ∈, $X^a$ to $X^d$ preferably each independently represent a fluorine atom. When an importance is given to the viscosity, $X^d$ preferably represents a hydrogen atom. When an importance is given to the balance among the viscosity, Δ∈, and the storage stability, $X^a$ to $X^c$ preferably represent a fluorine atom and $X^d$ preferably represents a hydrogen atom.

When an importance is given to the solubility, n preferably represents 0. When an importance is given to $T_{ni}$, n preferably represents 1.

In the compound represented by the general formula (1), heteroatoms are not directly bonded to each other.

Specific examples of preferred compounds are shown below, but the present invention is not limited thereto. The compound represented by the general formula (1) preferably includes compounds represented by general formula (1-1) to general formula (1-64).

[Chem. 6]
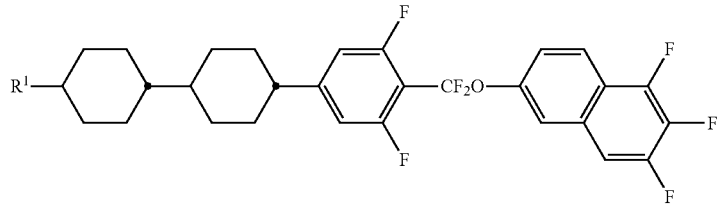
(1-1)
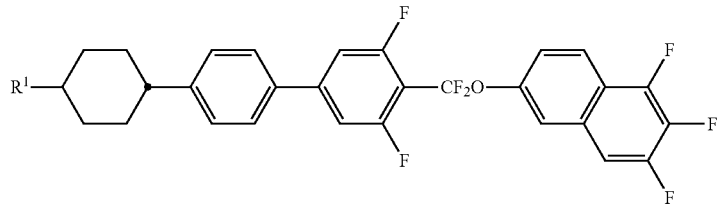
(1-2)
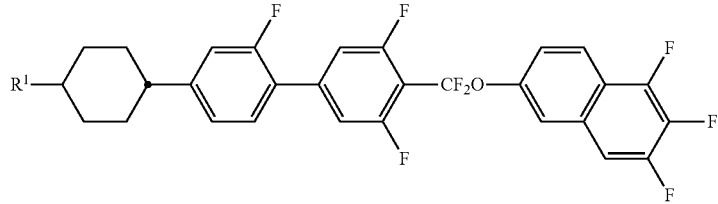
(1-3)
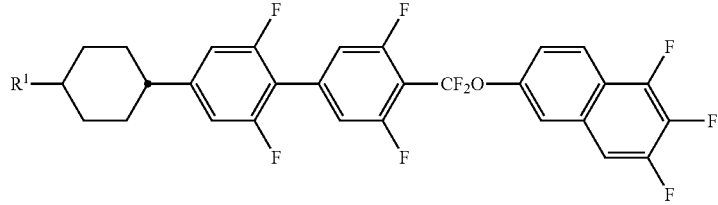
(1-4)
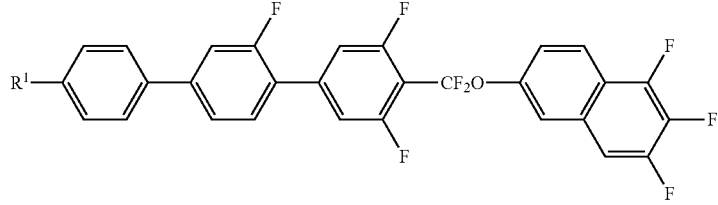
(1-5)
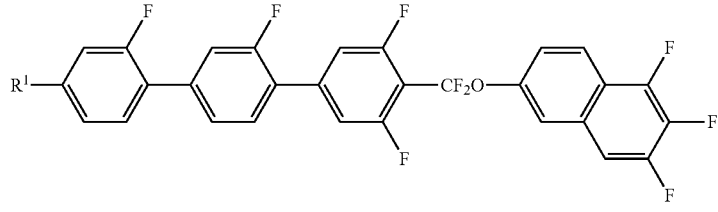
(1-6)
[Chem. 7]
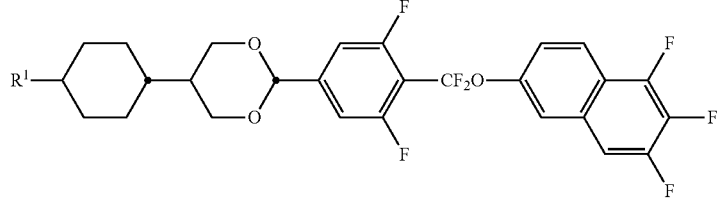
(1-7)

-continued
(1-8)
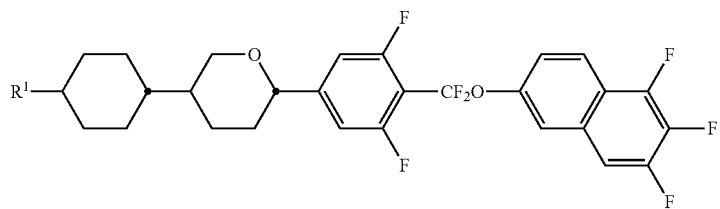
(1-9)
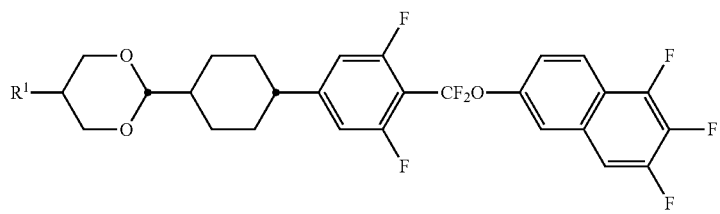
(1-10)
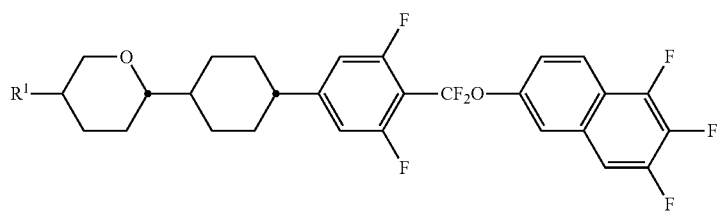
(1-11)
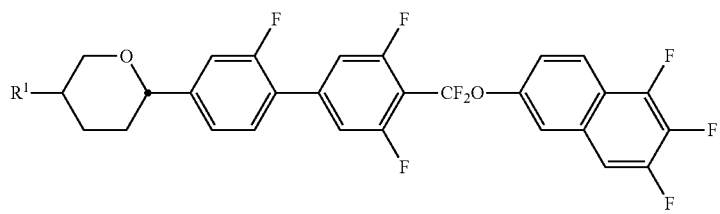
[Chem. 8]
(1-12)
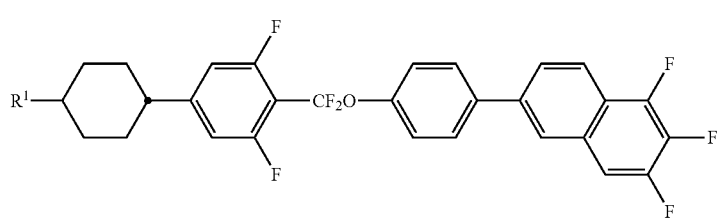
(1-13)
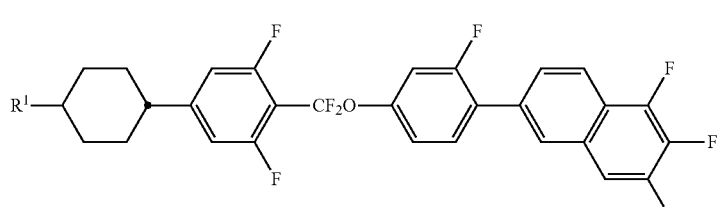
(1-14)
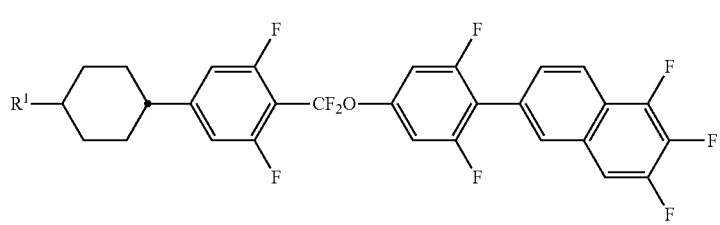

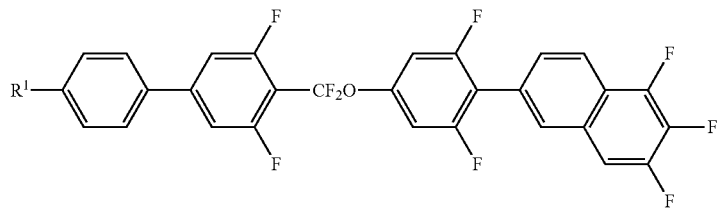
(1-15)
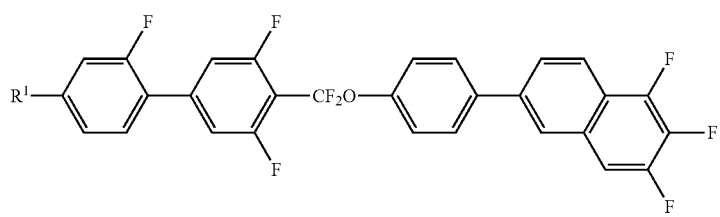
(1-16)
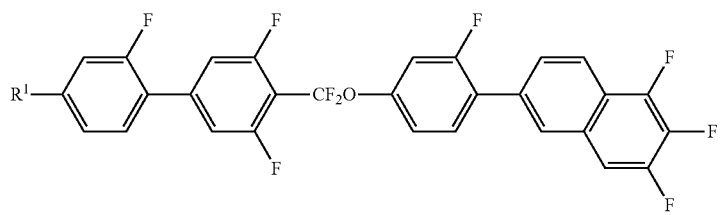
(1-17)
[Chem. 9]
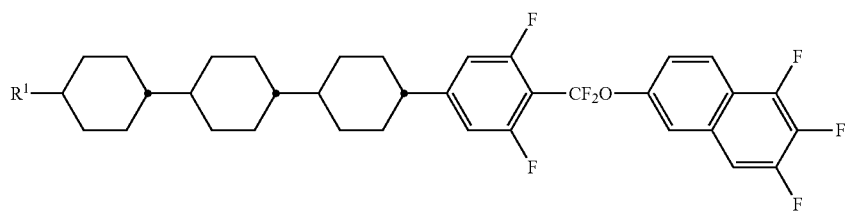
(1-18)
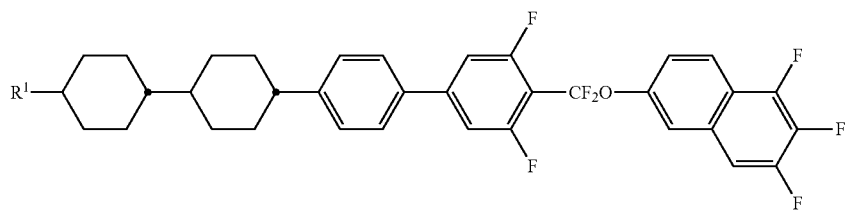
(1-19)
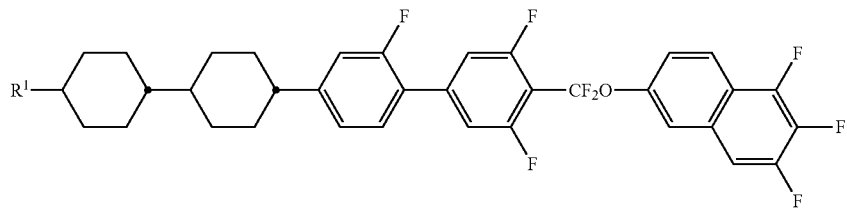
(1-20)
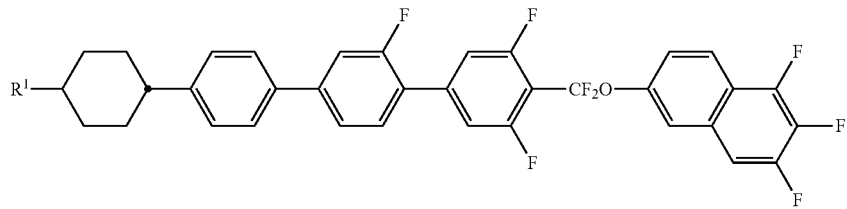
(1-21)

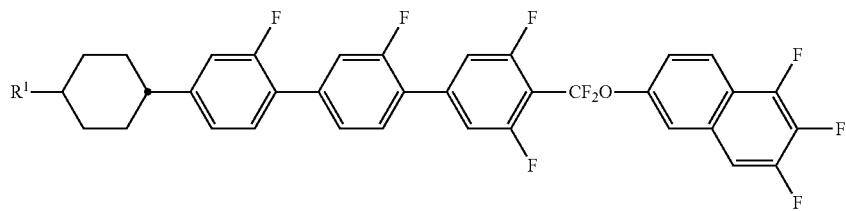
(1-22)
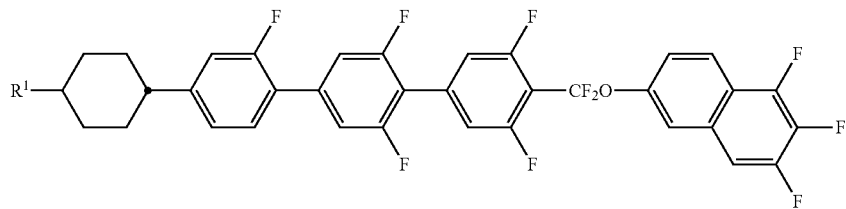
(1-23)
[Chem. 10]
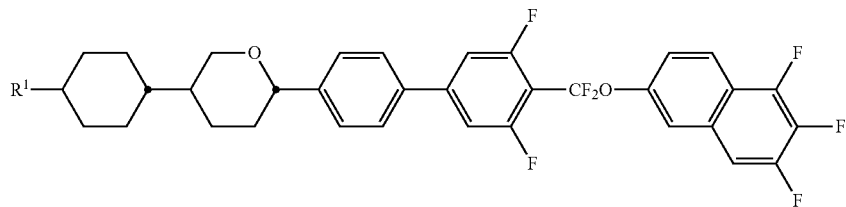
(1-24)
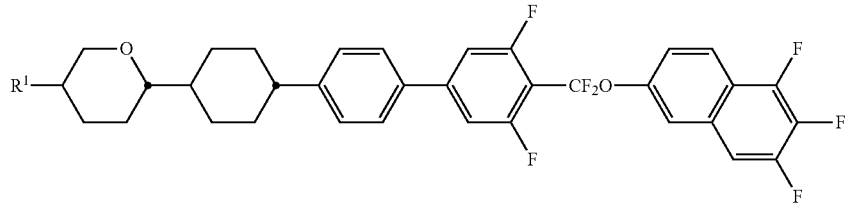
(1-25)
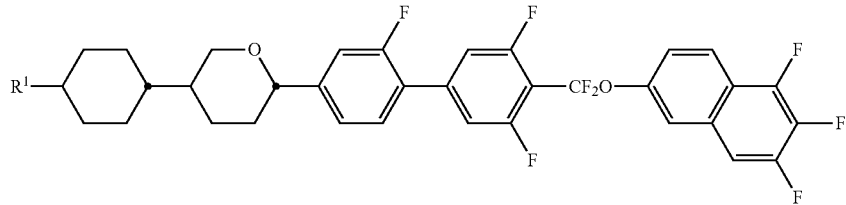
(1-26)
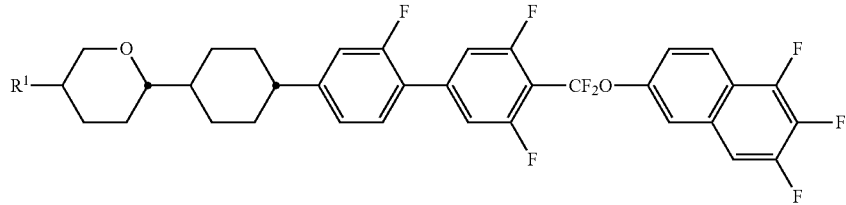
(1-27)
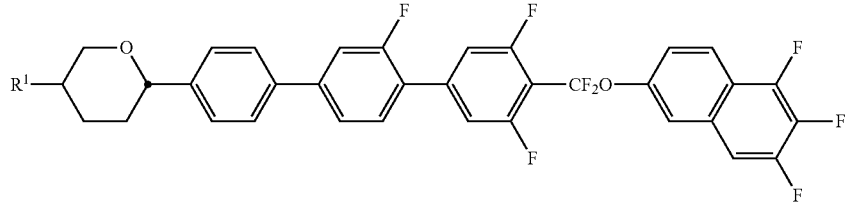
(1-28)

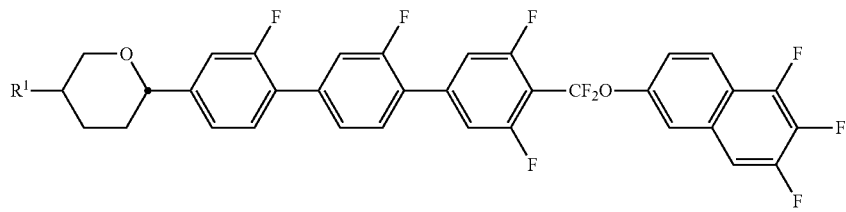
(1-29)
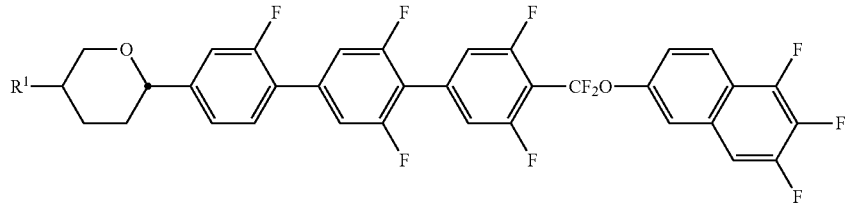
(1-30)
[Chem. 11]
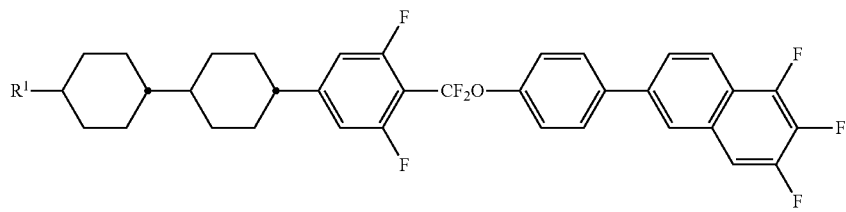
(1-31)
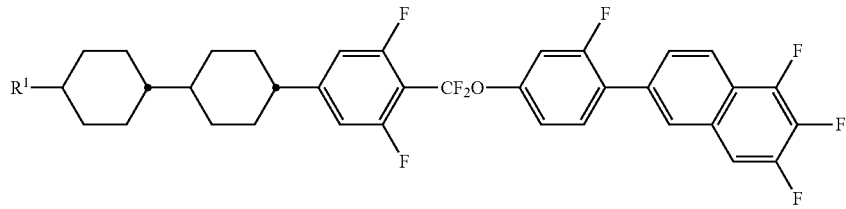
(1-32)
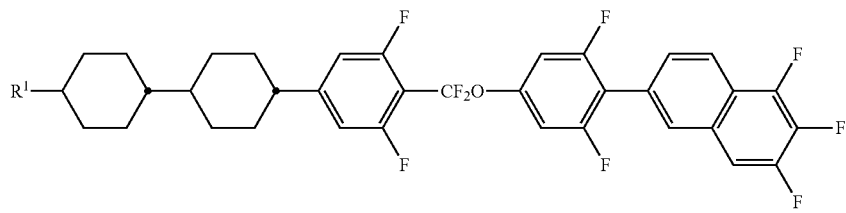
(1-33)
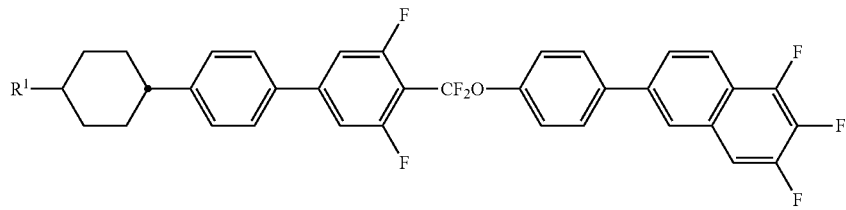
(1-34)
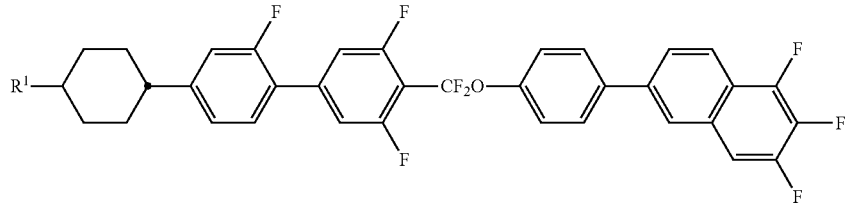
(1-35)

(1-36)
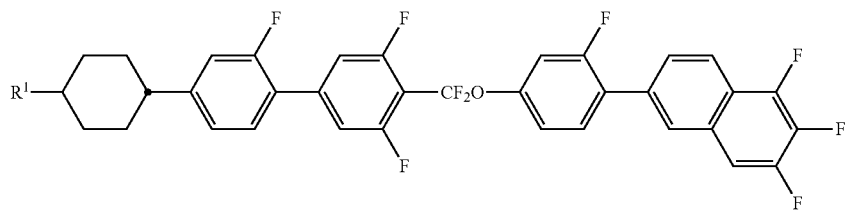
[Chem. 12]
(1-37)
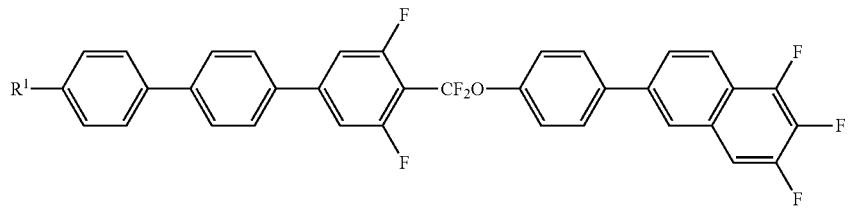
(1-38)
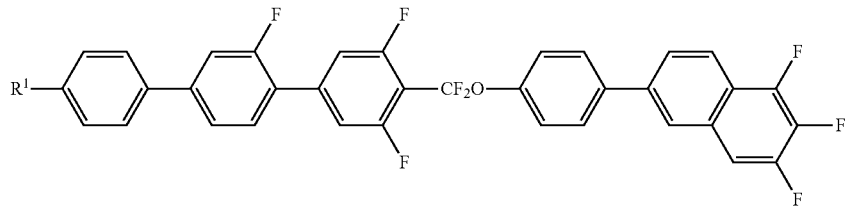
(1-39)
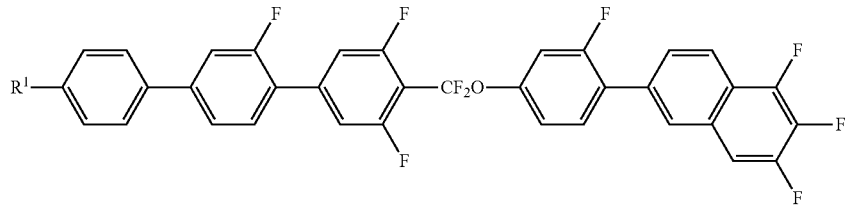
(1-40)
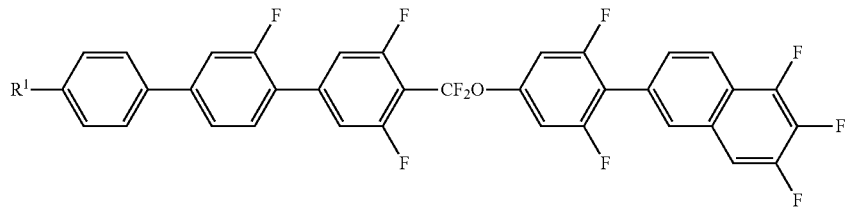
(1-41)
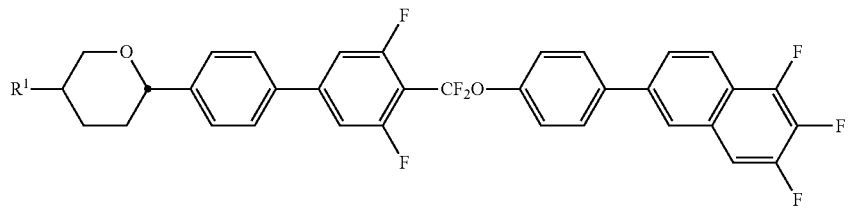
(1-42)
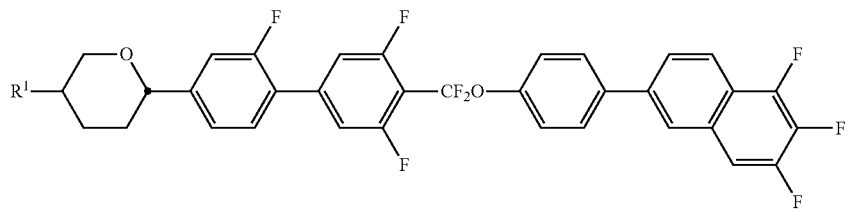

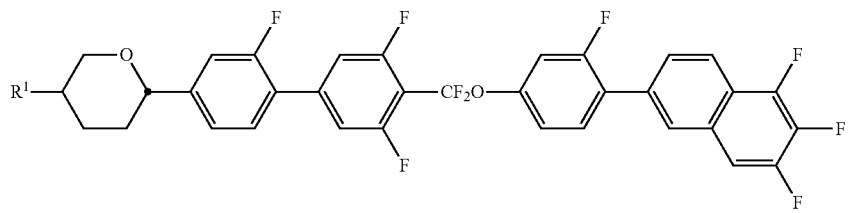
(1-43)
[Chem. 13]
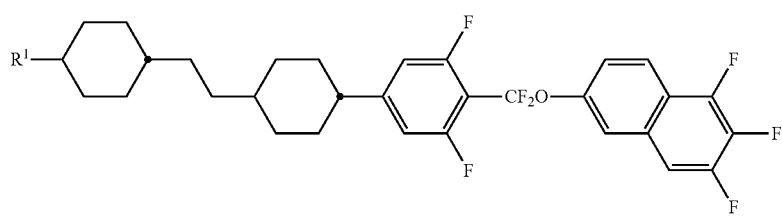
(1-44)
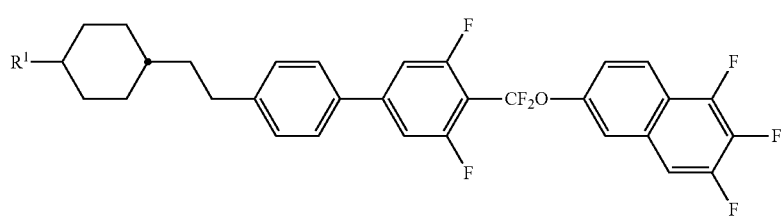
(1-45)
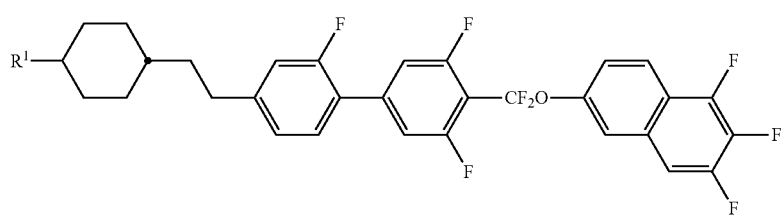
(1-46)
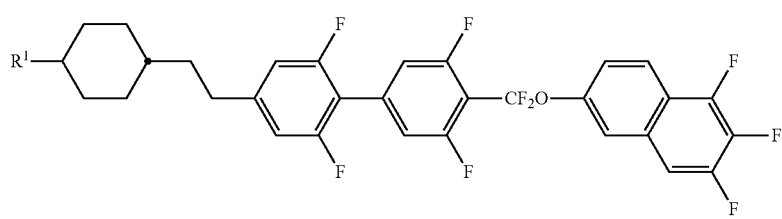
(1-47)
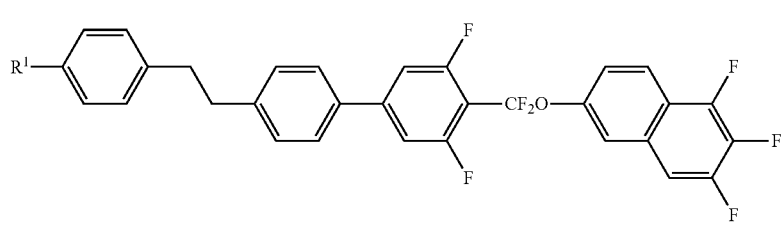
(1-48)
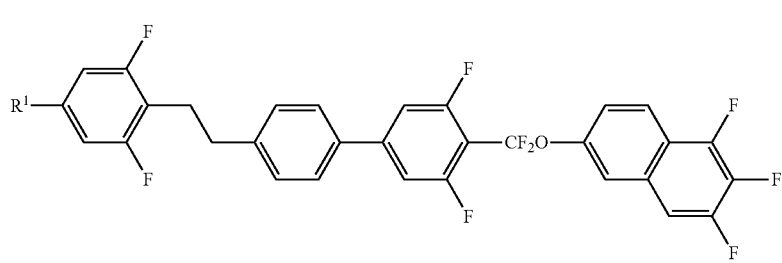
(1-49)

(1-50)
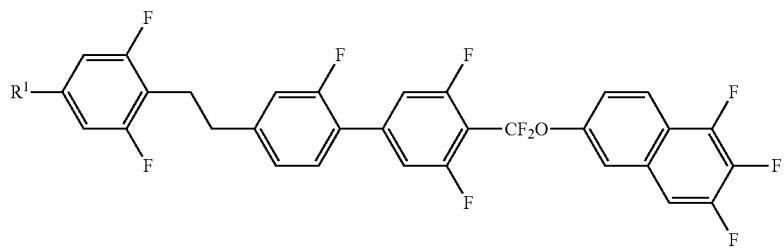
[Chem. 14]
(1-51)
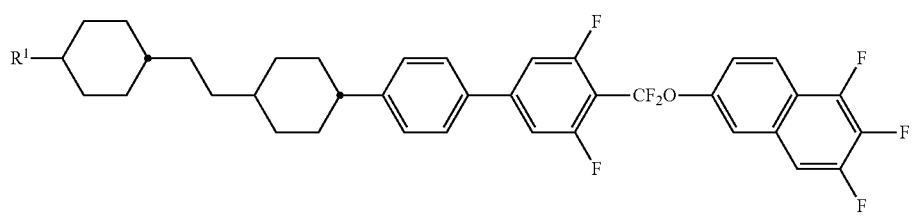
(1-52)
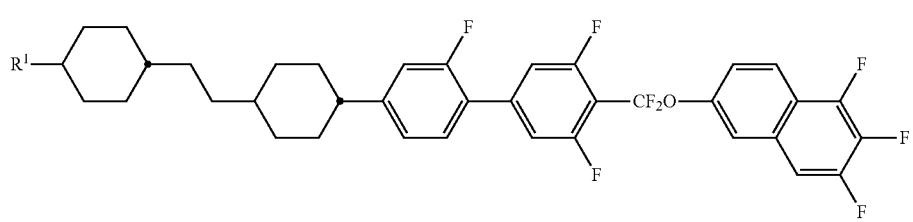
(1-53)
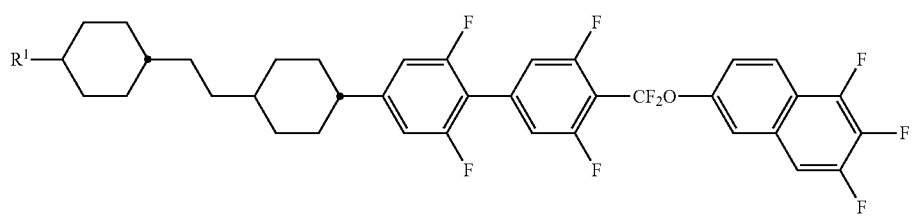
(1-54)
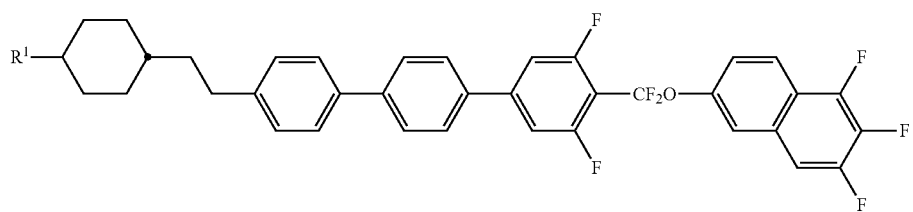
(1-55)
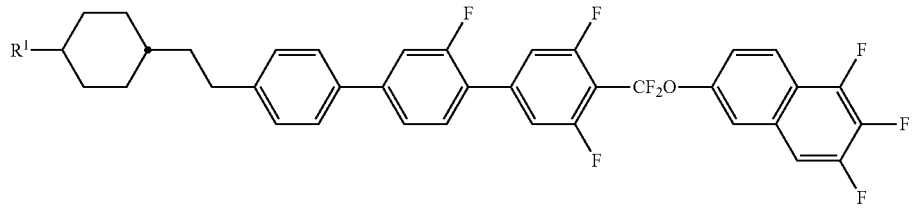
(1-56)
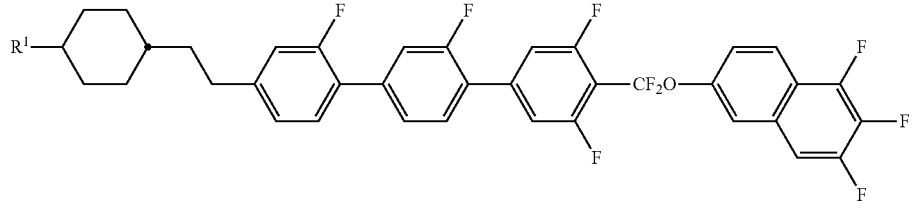

[Chem. 15]
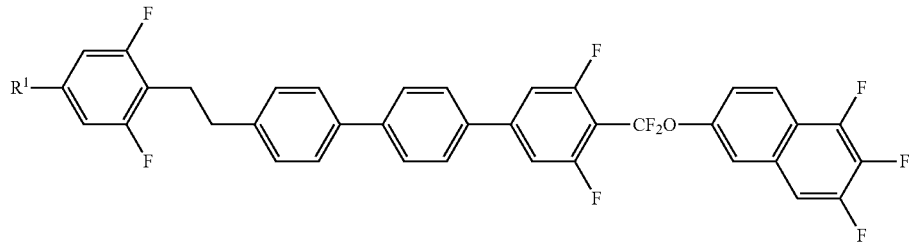
(1-57)
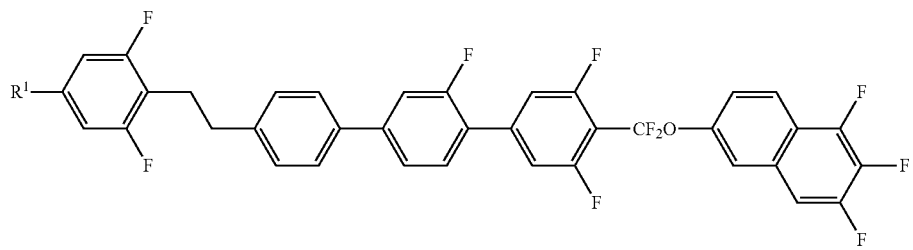
(1-58)
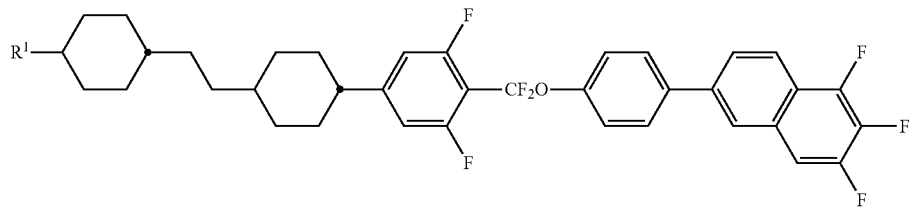
(1-59)
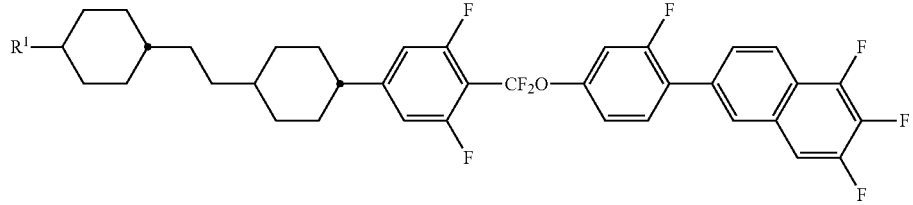
(1-60)
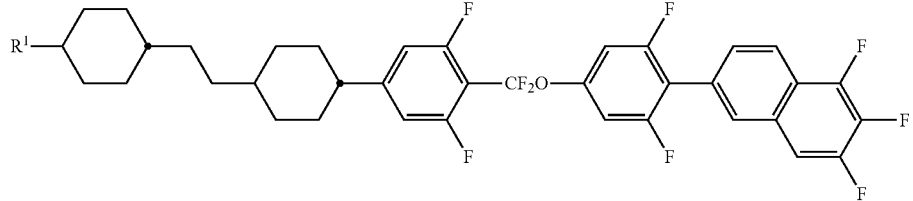
(1-61)
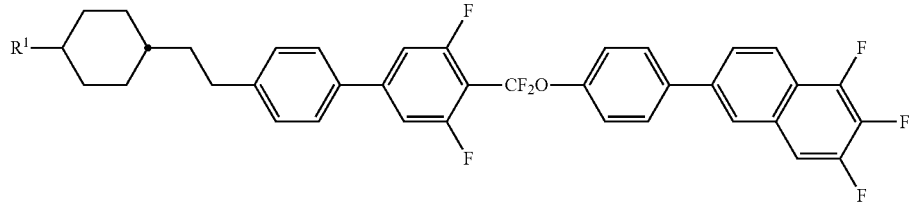
(1-62)
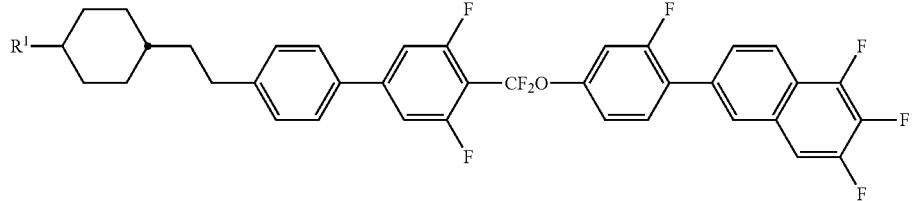
(1-63)

(1-64)

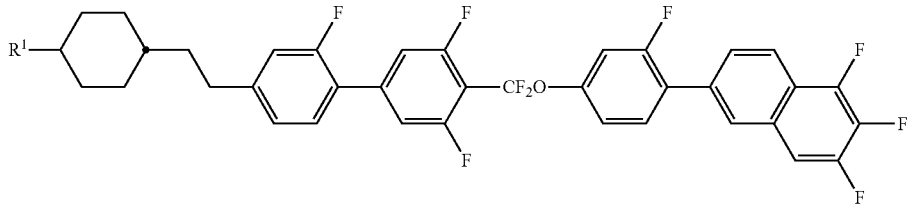

(In the formulae, $R^1$ each independently represent an alkyl group having 1 to 15 carbon atoms, an alkenyl group having 2 to 15 carbon atoms, an alkoxy group having 1 to 15 carbon atoms, or an alkenyloxy group having 2 to 15 carbon atoms.)

In the liquid crystal composition of the present invention, if the content of the compound represented by the general formula (1) is low, the effects are not produced. Therefore, the lower limit of the content of the compound in the liquid crystal composition is preferably 1% (% in the composition refers to mass % and the same applies hereafter), more preferably 2%, and further preferably 5%. If the content is high, a problem such as precipitation is caused. Therefore, the upper limit of the content is preferably 50%, more preferably 30%, further preferably 20%, and particularly preferably 10%. The compounds represented by the general formula (1) may be used alone or in combination of two or more.

To adjust the physical properties of the liquid crystal composition, a compound other than the compound represented by the general formula (1) may be used. A compound not having a liquid crystal phase may optionally added, in addition to the compound having a liquid crystal phase.

Preferred examples of the compounds that can be used as a mixture with the compounds represented by the general formula (1) are described below. In the composition provided by the present invention, at least one of the compounds represented by the general formula (1) is contained as a first component, and at least one of the following second to sixth components is particularly preferably contained as another component.

That is, the second component is a so-called fluorine-based (halogen-based) p-type liquid crystal compound. Examples of the p-type liquid crystal compound include compounds represented by general formulae (A1) to (A3).

[Chem. 16]

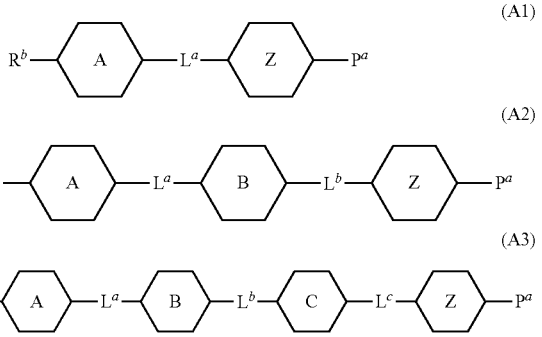

In the above formulae, $R^b$ represent an alkyl group having 1 to 12 carbon atoms, and may have a linear or branched structure or a cyclic structure with a three to six-membered ring; —$CH_2$— present in the group may be substituted with —O—, —CH=CH—, —CH=CF—, —CF=CH—, —CF=CF—, or —C≡C—; and a hydrogen atom present in the group may be substituted with a fluorine atom or a trifluoromethoxy group. $R^b$ preferably represent a linear alkyl group having 1 to 7 carbon atoms, a linear 1-alkenyl group having 2 to 7 carbon atoms, a linear 3-alkenyl group having 4 to 7 carbon atoms, or an alkyl group which has 1 to 5 carbon atoms and whose terminal is substituted with an alkoxy group having 1 to 3 carbon atoms. If an asymmetric carbon atom is present due to the branched structure, the compound may be an optically active compound or a racemic body.

Ring A, Ring B, and Ring C each independently represent a trans-1,4-cyclohexylene group, a transdecahydronaphthalene-trans-2,6-diyl group, a 1,4-phenylene group that may be substituted with one or more fluorine atoms, a naphthalene-2,6-diyl group that may be substituted with one or more fluorine atoms, a tetrahydronaphthalene-2,6-diyl group that may be substituted with one or more fluorine atoms, a 1,4-cyclohexenylene group that may be substituted with a fluorine atom, a 1,3-dioxane-trans-2,5-diyl group, a pyrimidine-2,5-diyl group, or a pyridine-2,5-diyl group. Ring A, Ring B, and Ring C preferably each independently represent a trans-1,4-cyclohexylene group, a transdecahydronaphthalene-trans-2,6-diyl group, a naphthalene-2,6-diyl group that may be substituted with a fluorine atom, or a 1,4-phenylene group that may be substituted with one or two fluorine atoms. In particular, when Ring B represents a trans-1,4-cyclohexylene group or a transdecahydronaphthalene-trans-2,6-diyl group, Ring A preferably represents a trans-1,4-cyclohexylene group. When Ring C represents a trans-1,4-cyclohexylene group or a transdecahydronaphthalene-trans-2,6-diyl group, Ring B and Ring A preferably represent a trans-1,4-cyclohexylene group. In the general formula (A3), Ring A preferably represents a trans-1,4-cyclohexylene group.

$L^a$, $L^b$, and $L^c$ are linking groups and each independently represent a single bond, an ethylene group (—$CH_2CH_2$—), a 1,2-propylene group (—CH($CH_3$)$CH_2$— and —$CH_2$CH($CH_3$)—), a 1,4-butylene group, —COO—, —OCO—, —$OCF_2$—, —$CF_2O$—, —CH=CH—, —CH=CF—, —CF=CH—, —CF=CF—, —C≡C—, or —CH=NN=CH—. $L^a$, $L^b$, and $L^c$ preferably each independently represent a single bond, an ethylene group, a 1,4-butylene group, —COO—, —$OCF_2$—, —$CF_2O$—, —CF=CF—, or —C≡C— and particularly preferably each independently represent a single bond or an ethylene group. In the general formula (A2), at least one of $L^a$, $L^b$, and $L^c$ preferably represents a single bond. In the general formula (A3), at least two of $L^a$, $L^b$, and $L^c$ preferably represent a single bond.

Ring Z is an aromatic ring and represents one of structures represented by general formulae (La) to (Lc) below.

[Chem. 17]

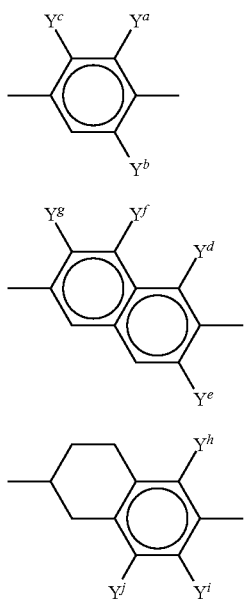

(La)

(Lb)

(Lc)

In the formulae, $Y^a$ to $Y^j$ each independently represent a hydrogen atom or a fluorine atom. In the general formula (La), at least one of $Y^a$ and $Y^b$ preferably represents a fluorine atom. In the general formula (Lb), at least one of $Y^d$ to $Y^f$ preferably represents a fluorine atom and $Y^d$ particularly preferably represents a fluorine atom. In the general formula (Lc), at least one of $Y^h$ and $Y^i$ preferably represents a fluorine atom and $Y^h$ particularly preferably represents a fluorine atom.

The terminal group $P^a$ represents a fluorine atom, a chlorine atom, a trifluoromethoxy group, a difluoromethoxy group, a trifluoromethyl group, a difluoromethyl group, an alkoxy group having 2 or 3 carbon atoms and substituted with two or more fluorine atoms, an alkyl group having 2 or 3 carbon atoms and substituted with two or more fluorine atoms, an alkenyl group having 2 or 3 carbon atoms and substituted with two or more fluorine atoms, or an alkenyloxy group having 2 or 3 carbon atoms and substituted with two or more fluorine atoms. The terminal group $P^a$ preferably represents a fluorine atom, a trifluoromethoxy group, or a difluoromethoxy group and particularly preferably represents a fluorine atom.

The third component is a so-called cyano-based p-type liquid crystal compound. Examples of the p-type liquid crystal compound include compounds represented by general formulae (B1) to (B3) below.

[Chem. 18]

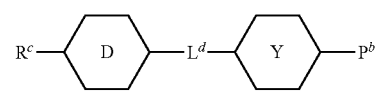

(B1)

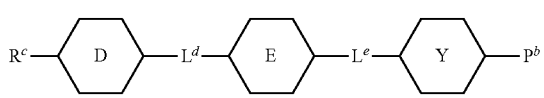

(B2)

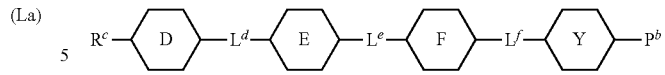

(B3)

In the above formulae, $R^c$ represent an alkyl group having 1 to 12 carbon atoms, and may have a linear or branched structure or a cyclic structure with a three to six-membered ring; —$CH_2$— present in the group may be substituted with —O—, —CH=CH—, —CH=CF—, —CF=CH—, —CF=CF—, or —C≡C—; and a hydrogen atom present in the group may be substituted with a fluorine atom or a trifluoromethoxy group. $R^c$ preferably represent a linear alkyl group having 1 to 7 carbon atoms, a linear 1-alkenyl group having 2 to 7 carbon atoms, a linear 3-alkenyl group having 4 to 7 carbon atoms, or an alkyl group which has 1 to 5 carbon atoms and whose terminal is substituted with an alkoxy group having 1 to 3 carbon atoms. If an asymmetric carbon atom is present due to the branched structure, the compound may be an optically active compound or a racemic body.

Ring D, Ring E, and Ring F each independently represent a trans-1,4-cyclohexylene group, a transdecahydronaphthalene-trans-2,6-diyl group, a 1,4-phenylene group that may be substituted with one or more fluorine atoms, a naphthalene-2,6-diyl group that may be substituted with one or more fluorine atoms, a tetrahydronaphthalene-2,6-diyl group that may be substituted with one or more fluorine atoms, a 1,4-cyclohexenylene group that may be substituted with a fluorine atom, a 1,3-dioxane-trans-2,5-diyl group, a pyrimidine-2,5-diyl group, or a pyridine-2,5-diyl group. Ring D, Ring E, and Ring F preferably each independently represent a trans-1,4-cyclohexylene group, a transdecahydronaphthalene-trans-2,6-diyl group, a naphthalene-2,6-diyl group that may be substituted with a fluorine atom, or a 1,4-phenylene group that may be substituted with one or two fluorine atoms. In particular, when Ring E represents a trans-1,4-cyclohexylene group or a transdecahydronaphthalene-trans-2,6-diyl group, Ring D preferably represents a trans-1,4-cyclohexylene group. When Ring F represents a trans-1,4-cyclohexylene group or a transdecahydronaphthalene-trans-2,6-diyl group, Ring D and Ring E preferably represent a trans-1,4-cyclohexylene group. In the general formula (B3), Ring D preferably represents a trans-1,4-cyclohexylene group.

$L^d$, $L^e$, and $L^f$ are linking groups and each independently represent a single bond, an ethylene group (—$CH_2CH_2$—), a 1,2-propylene group (—$CH(CH_3)CH_2$— and) —$CH_2CH(CH_3)$—), a 1,4-butylene group, —COO—, —OCO—, —$OCF_2$—, —$CF_2O$—, —CH=CH—, —CH=CF—, —CF=CH—, —CF=CF—, —C≡C—, —$OCH_2$—, —$CH_2O$—, or —CH=NN=CH—. $L^d$, $L^e$, and $L^f$ preferably each independently represent a single bond, an ethylene group, —COO—, —$OCF_2$—, —$CF_2O$—, —CF=CF—, or —C≡C— and particularly preferably each independently represent a single bond, an ethylene group, or —COO—. In the general formula (B2), at least one of $L^d$, $L^e$, and $L^f$ preferably represents a single bond. In the general formula (B3), at least two of $L^d$, $L^e$, and $L^f$ preferably represent a single bond.

$P^b$ represents a cyano group.

Ring Y is an aromatic ring and represents one of structures represented by general formulae (Ld) to (Lf) below.

[Chem. 19]

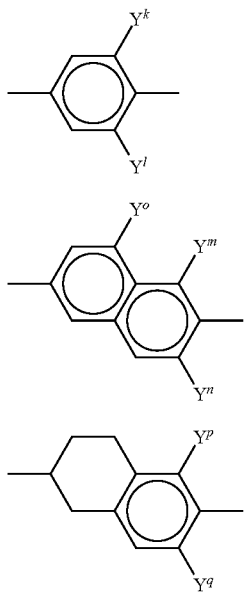

(Ld)

(Le)

(Lf)

In the formulae, $Y^k$ to $Y^q$ each independently represent a hydrogen atom or a fluorine atom. In the general formula (Ld), at least one of $Y^k$ and $Y^l$ preferably represents a fluorine atom. In the general formula (Le), at least one of $Y^m$ to $Y^o$ preferably represents a fluorine atom and $Y^m$ particularly preferably represents a fluorine atom. In the general formula (Lf), at least one of $Y^p$ and $Y^q$ preferably represents a fluorine atom and $Y^p$ particularly preferably represents a fluorine atom.

The fourth component is a so-called nonpolar liquid crystal compound, which has a dielectric anisotropy of about 0. Examples of the nonpolar liquid crystal compound include compounds represented by general formulae (C1) to (C3) below.

[Chem. 20]

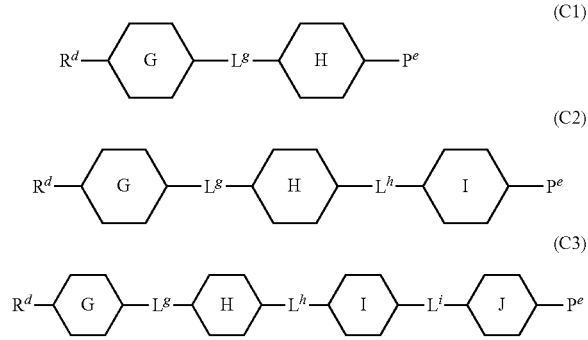

(C1)

(C2)

(C3)

In the above formulae, $R^d$ and $P^e$ each independently represent an alkyl group having 1 to 12 carbon atoms, and may have a linear or branched structure or a cyclic structure with a three to six-membered ring; —$CH_2$— present in the group may be substituted with —O—, —CH=CH—, —CH=CF—, —CF=CH—, —CF=CF—, or —C≡C—; and a hydrogen atom present in the group may be substituted with a fluorine atom or a trifluoromethoxy group. $R^d$ and $P^e$ preferably each independently represent a linear alkyl group having 1 to 7 carbon atoms, a linear 1-alkenyl group having 2 to 7 carbon atoms, a linear 3-alkenyl group having 4 to 7 carbon atoms, a linear alkoxy group having 1 to 3 carbon atoms, or a linear alkyl group which has 1 to 5 carbon atoms and whose terminal is substituted with an alkoxy group having 1 to 3 carbon atoms. Furthermore, at least one of $R^d$ and $P^e$ particularly preferably each independently represent a linear alkyl group having 1 to 7 carbon atoms, a linear 1-alkenyl group having 2 to 7 carbon atoms, or a linear 3-alkenyl group having 4 to 7 carbon atoms.

Ring G, Ring H, Ring I, and Ring J each independently represent a trans-1,4-cyclohexylene group, a transdecahydronaphthalene-trans-2,6-diyl group, a 1,4-phenylene group that may be substituted with 1 or 2 fluorine atoms or a methyl group, a naphthalene-2,6-diyl group that may be substituted with one or more fluorine atoms, a tetrahydronaphthalene-2,6-diyl group that may be substituted with 1 or 2 fluorine atoms, a 1,4-cyclohexenylene group that may be substituted with 1 or 2 fluorine atoms, a 1,3-dioxane-trans-2,5-diyl group, a pyrimidine-2,5-diyl group, or a pyridine-2,5-diyl group. In each of the compounds, the number of the trans-decahydronaphthalene-trans-2,6-diyl group, the naphthalene-2,6-diyl group that may be substituted with one or more fluorine atoms, the tetrahydronaphthalene-2,6-diyl group that may be substituted with 1 or 2 fluorine atoms, the 1,4-cyclohexenylene group that may be substituted with a fluorine atom, the 1,3-dioxane-trans-2,5-diyl group, the pyrimidine-2,5-diyl group, and the pyridine-2,5-diyl group is preferably one or less. Other rings are each preferably a trans-1,4-cyclohexylene group or a 1,4-phenylene group that may be substituted with 1 or 2 fluorine atoms or a methyl group. The total number of fluorine atoms present in Ring G, Ring H, Ring I, and Ring J is preferably 2 or less and more preferably 0 or 1.

$L^g$, $L^h$, and $L^i$ are linking groups and each independently represent a single bond, an ethylene group (—$CH_2CH_2$—), a 1,2-propylene group (—$CH(CH_3)CH_2$— and) —$CH_2CH(CH_3)$—), a 1,4-butylene group, —COO—, —OCO—, —$OCF_2$—, —$CF_2O$—, —CH=CH—, —CH=CF—, —CF=CH—, —CF=CF—, —C≡C—, or —CH=NN=CH—. $L^g$, $L^h$, and $L^i$ preferably each independently represent a single bond, an ethylene group, a 1,4-butylene group, —COO—, —OCO—, —$OCF_2$—, —$CF_2O$—, —CF=CF—, —C≡C—, or —CH=NN=CH—. In the general formula (C2), at least one of $L^g$, $L^h$, and $L^i$ preferably represents a single bond. In the general formula (C3), at least two of $L^g$, $L^h$, and $L^i$ preferably represent a single bond.

The compounds represented by the general formulae (C1) to (C3) exclude the compounds represented by the general formulae (A1) to (A3) and the compounds represented by the general formulae (B1) to (B3).

In the compounds represented by the general formulae (A1) to (A3), the compounds represented by the general formulae (B1) to (B3), and the compounds represented by the general formulae (C1) to (C3), heteroatoms are not directly bonded to each other.

The fifth component is an optically active compound used to induce a helical structure in the liquid crystal composition. The fifth component is preferably a compound having an asymmetric carbon atom and more preferably a compound having a 1-methylheptyloxy group.

The sixth component is a compound having a polymerizable functional group that allows polymerization by applying ultraviolet rays or heat, the compound being added in order to improve the response speed or to improve the alignment properties of the liquid crystal composition. The polymerizable group is preferably an acryloxy group or a methacryloxy group and more preferably a methacryloxy group. Furthermore, the compound preferably has 1 to 3 polymerizable functional groups and more preferably has 2 polymerizable functional groups.

In the present invention, the compound represented by the general formula (1) can be produced by the following method. Obviously, the spirit and scope of the present invention are not limited by the production examples.

(Production Method 1)

A compound represented by general formula (2),

[Chem. 21]

$$R-[A^1-Z^1]_n-A^2-Z^2-A^3-Z^3-A^4 \quad (2)$$

(in the formula, R, $A^1$ to $A^3$, $Z^1$ to $Z^3$, and n are each independently the same as R, $A^1$ to $A^3$, $Z^1$ to $Z^3$, and n in the general formula (1); and $A^4$ represents a 3-fluorophenyl group or a 3,5-difluorophenyl group), is caused to act on a base and then reacted with dibromodifluoromethane to obtain a compound represented by general formula (3).

[Chem. 22]

$$R-[A^1-Z^1]_n-A^2-Z^2-A^3-Z^3-A^4-CF_2Br \quad (3)$$

(In the formula, R, $A^1$ to $A^3$, $Z^1$ to $Z^3$, and n are each independently the same as R, $A^1$ to $A^3$, $Z^1$ to $Z^3$, and n in the general formula (1); and $A^4$ represents a 3-fluorophenyl group or a 3,5-difluorophenyl group.)

Any solvent that causes the reaction to suitably proceed may be used, but the solvent is preferably an ether solvent such as tetrahydrofuran or diethyl ether. These solvents may be used alone or in the form of a mixture.

Any base that causes the reaction to suitably proceed may be used, but the base is preferably an alkyllithium reagent such as n-butyllithium, sec-butyllithium, or tert-butyllithium or a lithium amide such as lithium diisopropylamide. When $A^4$ represents a 3-fluorophenyl group, sec-butyllithium is more preferably used. When $A^4$ represents a 3,5-difluorophenyl group, n-butyllithium or lithium diisopropylamide is more preferably used.

Any reaction temperature that causes the reaction to suitably proceed may be employed, but the reaction temperature is preferably −76° to −40° C. and more preferably −76° C. to −60° C. After the addition of dibromodifluoromethane, the reaction is preferably caused to proceed at room temperature.

Subsequently, the compound represented by the general formula (3) is reacted with a compound represented by general formula (4),

[Chem. 23]

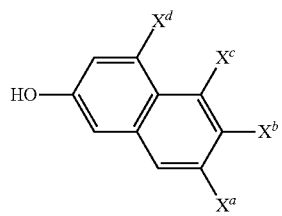

(4)

(in the formula, $X^a$ to $X^d$ are each independently the same as $X^a$ to $X^d$ in the general formula (1)), in the presence of a base to obtain a compound represented by the general formula (1) in which $A^4$ represents 3-fluoro-1,4-phenylene or 3,5-difluoro-1,4-phenylene.

Any base that causes the reaction to suitably proceed may be used, but the base is preferably a carbonate such as sodium carbonate, potassium carbonate, or cesium carbonate or an alkali metal hydroxide such as sodium hydroxide or potassium hydroxide and more preferably potassium carbonate.

Any solvent that causes the reaction to smoothly proceed may be used, but the solvent is preferably an amide solvent such as N,N-dimethylformamide, N,N-dimethylacetamide, or N-methylpyrrolidone or an ether solvent such as tetrahydrofuran, 1,4-dioxane, or t-butyl methyl ether and more preferably N,N-dimethylformamide or N-methylpyrrolidone.

Any reaction temperature that causes the reaction to suitably proceed may be employed, but the reaction temperature is preferably room temperature to a temperature at which the solvent is refluxed, more preferably room temperature to 80° C., and particularly preferably 40° C. to 60° C.

(Production Method 2)

A compound represented by general formula (5),

[Chem. 24]

$$R-[A^1-Z^1]_n-A^2-Z^2-A^3-Z^3-A^4-COOH \quad (5)$$

(in the formula, R, $A^1$ to $A^4$, $Z^1$ to $Z^3$, and n are the same as $A^1$ to $A^4$ and $Z^1$ to $Z^3$ in the general formula (1)), is reacted with an acid chloride to obtain a compound represented by general formula (6).

[Chem. 25]

$$R-[A^1-Z^1]_n-A^2-Z^2-A^3-Z^3-A^4-COCl \quad (6)$$

(In the formula, R, $A^1$ to $A^4$, $Z^1$ to $Z^3$, and n are the same as $A^1$ to $A^4$ and $Z^1$ to $Z^3$ in the general formula (1).)

Any acid chloride that causes the reaction to suitably proceed may be used, but the acid chloride is preferably oxalic acid dichloride or thionyl chloride.

Any solvent that causes the reaction to suitably proceed may be used, but the solvent is preferably a chlorine-based solvent such as dichloromethane, chloroform, carbon tetrachloride, or 1,2-dichloroethane, a hydrocarbon solvent such as hexane or toluene, or an ether solvent such as diethyl ether or tetrahydrofuran and more preferably dichloromethane or 1,2-dichloroethane.

Any reaction temperature that causes the reaction to suitably proceed may be employed, but the reaction temperature is preferably 0° C. to a temperature at which the solvent is refluxed and more preferably 40° C. to a temperature at which the solvent is refluxed.

Subsequently, the compound represented by the general formula (6) is reacted with a dithiol and trifluoromethanesulfonic acid to obtain a compound represented by general formula (7).

[Chem. 26]

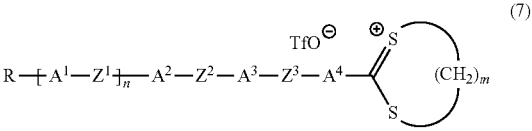

(7)

(In the formula, R, $A^1$ to $A^4$, $Z^1$ to $Z^3$, and n are the same as $A^1$ to $A^4$ and $Z^1$ to $Z^3$ in the general formula (1); and m represents 3 or 4.)

The dithiol is preferably 1,3-propanedithiol or 1,4-butanedithiol.

Any reaction temperature that causes the reaction to suitably proceed may be employed. However, when trifluoromethanesulfonic acid is added to a mixture of the compound represented by the general formula (6) and the dithiol, the reaction temperature is preferably 0° C. After that, the reaction temperature is preferably 100° C. to 130° C. and more preferably 110° C. to 120° C.

Subsequently, the compound represented by the general formula (7) is reacted with the compound represented by the general formula (4) in the presence of a fluorinating reagent and an oxidizing agent to obtain a compound represented by the general formula (1).

Any fluorinating reagent that causes the reaction to suitably proceed may be used, but the fluorinating reagent is preferably triethylamine trihydrofluoride, tetrabutylammonium dihydrogen trifluoride, a pyridine-hydrogen fluoride complex, or a melamine-hydrogen fluoride complex.

Any reaction temperature that causes the reaction to suitably proceed may be employed, but the reaction temperature is preferably −76° C. to −60° C.

EXAMPLES

Hereafter, the present invention will be further described in detail based on Examples, but is not limited to Examples.

The phase transition temperature was measured using both a polarizing microscope equipped with a temperature control stage and a differential scanning calorimeter (DSC).

In the compositions of Examples and Comparative Examples below, "%" means "mass %".

$T_{n-i}$ represents a nematic phase-isotropic phase transition temperature.

The following abbreviations are used to describe compounds.

THF: tetrahydrofuran

DMF: N,N-dimethylformamide

Me: methyl group, Pr: n-propyl group, Bu: n-butyl group

Tf: trifluoromethanesulfonyl group

Example 1

Production of [3,5-difluoro-trans-4-(4-(trans-4-propylcyclohexyl)cyclohexyl)phenyl]-(5,6,7-trifluoro-2-naphthyloxy)difluoromethane

[Chem. 27]

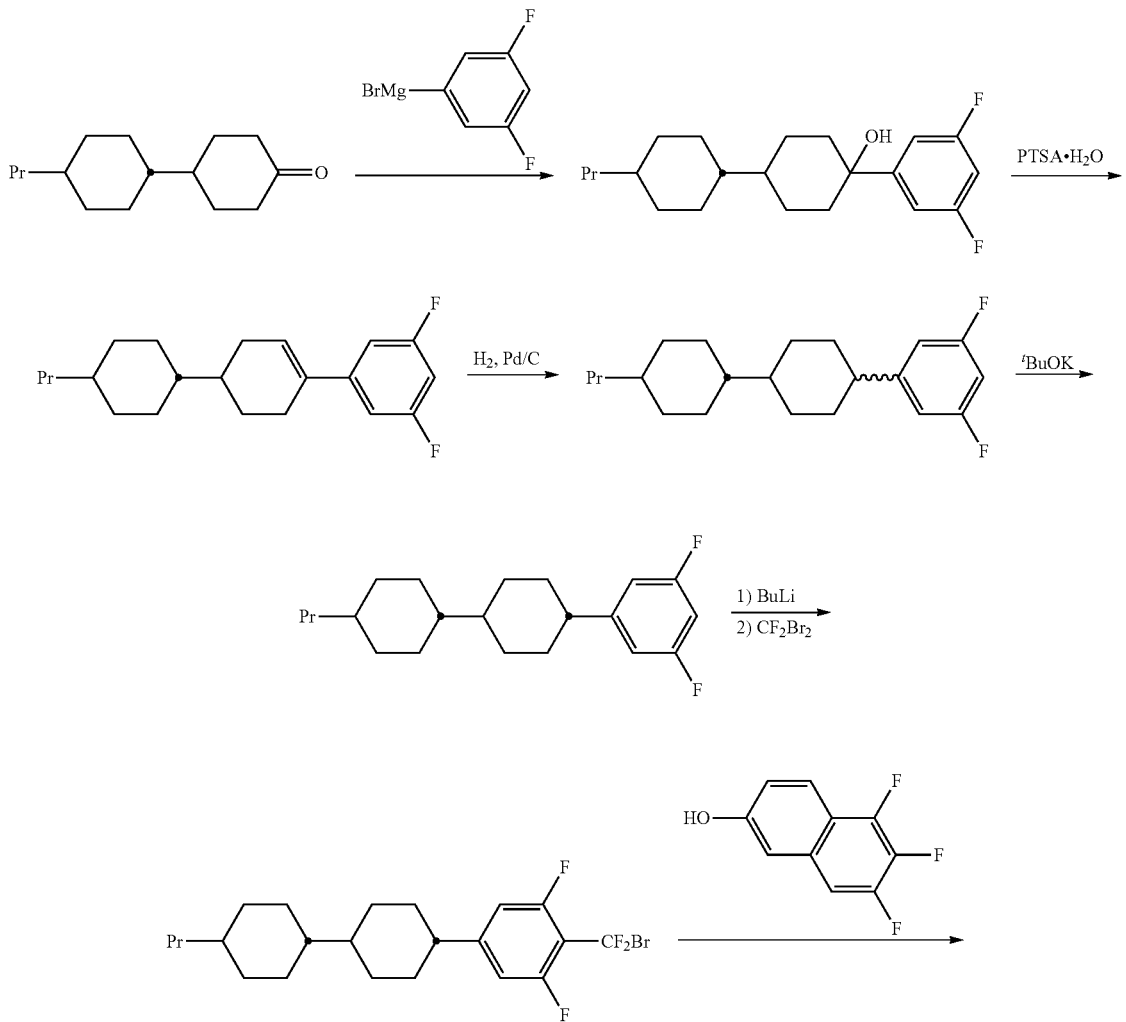

-continued

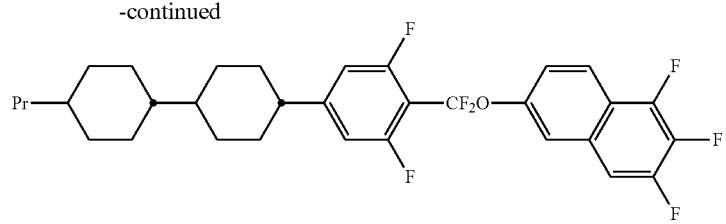

(1-1) In a nitrogen atmosphere, metal magnesium (5.5 g) was suspended in THF (5 mL), a solution prepared by dissolving 3,5-difluorobromobenzene (41.5 g) in THF (120 mL) was added at a rate at which the solution was gently refluxed, and stirring was performed at 40° C. for 45 minutes. Subsequently, a solution prepared by dissolving 4-(trans-4-propylcyclohexyl)cyclohexanone (39.8 g) in THF (85 mL) was added at 40° C., and then stirring was performed at room temperature for one hour. The reaction liquid was gently added under stirring to 10% hydrochloric acid (120 mL) cooled to 5° C., and toluene (160 mL) was added thereto and extraction was performed. The resulting organic layer was washed with a saturated saline solution (120 mL). Anhydrous sodium sulfate was added to perform drying. The organic solvent was distilled off under reduced pressure to obtain a crude 3,5-difluoro-4-(1-hydroxy-4-(4-trans-propylcyclohexyl)cyclohexyl)benzene (62.5 g).

(1-2) A solution prepared by dissolving the crude 3,5-difluoro-4-(1-hydroxy-4-(trans-4-propylcyclohexyl)cyclohexyl)benzene (62.5 g) obtained in (1-1) and p-toluenesulfonic acid monohydrate (1.7 g) in toluene (300 mL) was refluxed, and stirring was performed for five hours while water generated was removed using a Dean-Stark apparatus. The resulting mixture was naturally cooled, and water (150 mL) was added thereto. The mixture was separated and the resulting organic layer was washed with an aqueous saturated sodium hydrogen carbonate solution (150 mL) and a saturated saline solution (150 mL). Anhydrous sodium sulfate was added thereto to perform drying. The organic solvent was distilled off under reduced pressure, and the resulting residue was purified by alumina column chromatography to obtain a crude 3,5-difluoro-4-(4-(trans-4-propylcyclohexyl)-1-cyclohexenyl)benzene (64.1 g).

(1-3) A solution prepared by dissolving the crude 3,5-difluoro-4-(4-(trans-4-propylcyclohexyl)-1-cyclohexenyl)benzene (64.1 g) obtained in (1-2) and 5 wt % palladium/carbon (3.0 g) in toluene (200 mL) and ethanol (100 mL) was inserted into an autoclave, and stirring was performed in a hydrogen atmosphere (0.5 MPa) at 40° C. for five hours. The palladium/carbon was removed by filtration and the solvent was distilled off under reduced pressure to obtain a crude 3,5-difluoro-4-(4-(trans-4-propylcyclohexyl)-1-cyclohexyl)benzene (64.3 g).

(1-4) In a nitrogen atmosphere, the crude 3,5-difluoro-4-(4-(trans-4-propylcyclohexyl)cyclohexyl)benzene (64.3 g) obtained in (1-3) and potassium tert-butoxide (2.0 g) were dissolved in DMF (300 mL), and stirring was performed at 70° C. for three hours. After natural cooling, toluene (300 mL) and water (300 mL) were added thereto and the mixture was separated. The resulting organic layer was washed with water (300 mL) and a saturated saline solution (300 mL). Anhydrous sodium sulfate was added to perform drying, and the organic solvent was distilled off under reduced pressure. The resulting residue was purified by silica gel column chromatography, subjected to reduced-pressure distillation (0.7 mmHg, boiling point: 171 to 174° C.), and recrystallized using ethanol to obtain 3,5-difluoro-4-(trans-4-(trans-4-propylcyclohexyl)cyclohexyl)benzene (43.5 g).

(1-5) In a nitrogen atmosphere, a solution prepared by dissolving the 3,5-difluoro-4-(trans-4-(trans-4-propylcyclohexyl)cyclohexyl)benzene (43.5 g) obtained in (1-4) in THF (300 mL) was cooled to −76° C., and a 1.6 mol/L n-butyllithium/hexane solution (95 mL) was added thereto and stirring was performed at −76° C. for one hour. Subsequently, a solution prepared by dissolving dibromodifluoromethane (19.0 g) in THF (90 mL) was added thereto, and the temperature was gradually increased to room temperature. Toluene (300 mL) and water (200 mL) were added and the mixture was separated. The resulting organic layer was washed with a 10% aqueous sodium sulfite solution (150 mL) and a saturated saline solution (159 mL). Anhydrous sodium sulfate was added to perform drying, and the organic solvent was distilled off under reduced pressure. The resulting residue was purified by silica gel column chromatography to obtain a crude (3,5-difluoro-4-(trans-4-(trans-4-propylcyclohexyl)cyclohexyl)phenyl)bromodifluoromethane (57.5 g).

(1-6) 5,6,7-Trifluoro-2-naphthol (25.4 g, produced in conformity with Japanese Unexamined Patent Application Publication No. 2004-91361), the (3,5-difluoro-4-(trans-4-(trans-4-propylcyclohexyl)cyclohexyl)phenyl)bromodifluoromethane (57.5 g) obtained in (1-5), and anhydrous potassium carbonate (26.5 g) were suspended in DMF (300 mL), and stirring was performed at 50° C. for 18 hours. After natural cooling, water (200 mL) and toluene (200 mL) were added and the mixture was separated. The resulting organic layer was washed with a saturated saline solution (200 mL) twice. Anhydrous sodium sulfate was added to perform drying, and the organic solvent was distilled off under reduced pressure. The resulting residue was purified by silica gel column chromatography and recrystallized using ethanol and hexane to obtain [3,5-difluoro-4-(trans-4-(trans-4-propylcyclohexyl)cyclohexyl)phenyl]-(5,6,7-trifluoro-2-naphthyloxy)difluoromethane (47.4 g).

MS m/z: 566 [M$^+$]

$^1$HNMR (CDCl$_3$, TMS internal standard) δ (ppm)=8.03 (1H, d, J=9.2 Hz), 7.67 (1H, s), 7.48-7.46 (1H, m), 7.38-7.32 (1H, m), 7.19 (2H, d, 10.3 Hz), 2.35 (1H, tt, J$_1$=3.2 Hz, J$_2$=12.1 Hz), 1.90-1.71 (8H, m), 1.33-1.28 (4H, m), 1.56-0.94 (9H, m), 0.89-0.81 (5H, m)

Example 2

Production of [3,5-difluoro-4-(2-fluoro-4-(trans-4-propylcyclohexyl)phenyl)phenyl]-(5,6,7-trifluoro-2-naphthyloxy)difluoromethane

[Chem. 28]

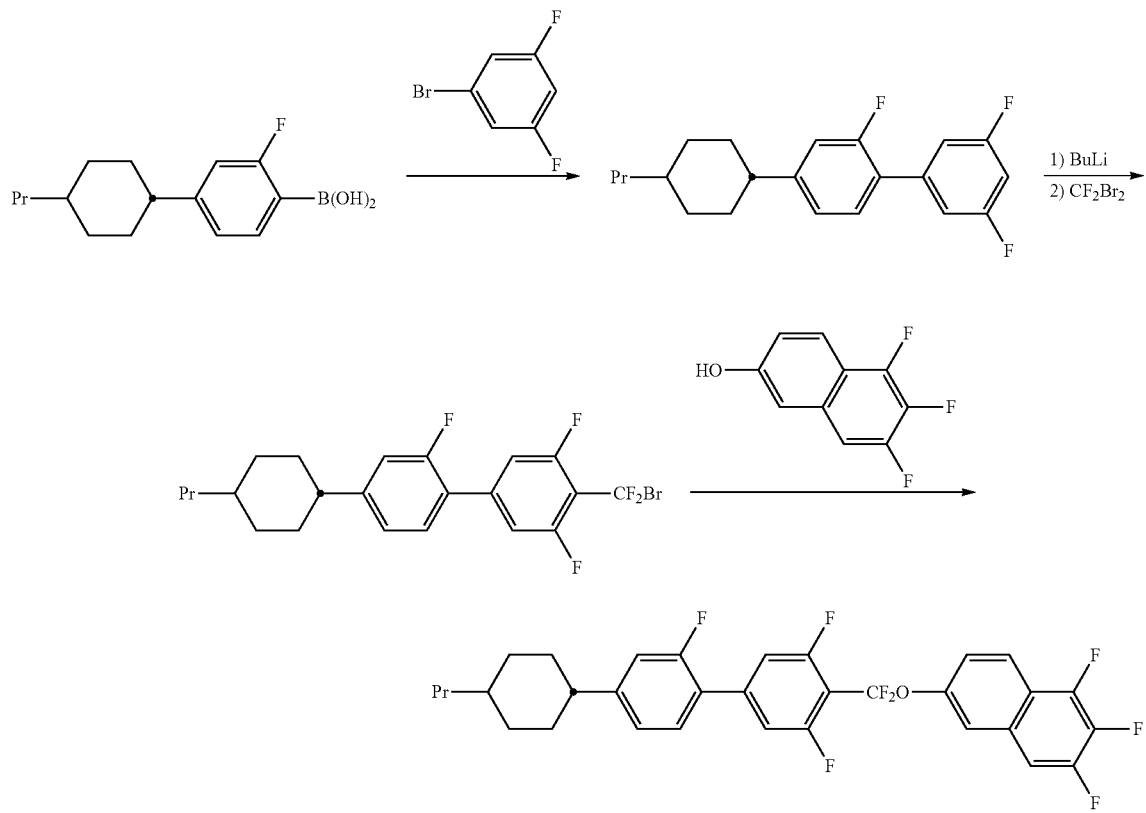

(2-1) 3,5-Difluorobromobenzene (30 g), tetrakis(triphenylphosphine)palladium (0) (1.8 g), ethanol (150 mL), and a 2 mol/L aqueous potassium carbonate solution (155 mL) were mixed with each other and heated to 50° C. A solution prepared by dissolving 2-fluoro-4-(trans-4-propylcyclohexyl)phenylboric acid (49.3 g) in ethanol (300 mL) was added thereto, and stirring was performed at 50° C. for five hours. After the temperature was decreased to room temperature by natural cooling, toluene (300 mL) was added thereto and the mixture was separated. The resulting organic layer was washed with a saturated saline solution (200 mL) twice. Anhydrous sodium sulfate was added to perform drying, and the organic solvent was distilled off under reduced pressure. The resulting residue was purified by silica gel column chromatography and recrystallized using ethanol to obtain 4-[2-fluoro-4-(trans-4-propylcyclohexyl)phenyl]-3,5-difluorobenzene (39.1 g).

(2-2) The subsequent processes were performed by the same method as in Example 1 to obtain [3,5-difluoro-4-(2-fluoro-4-(trans-4-propylcyclohexyl)phenyl)phenyl]-(5,6,7-trifluoro-2-naphthyloxy)difluoromethane (20.5 g).

MS m/z: 578 [M$^+$]

$^1$HNMR (CDCl$_3$, TMS internal standard) δ (ppm)=8.03 (1H, d, J=9.2 Hz), 7.67 (1H, s), 7.49-7.45 (1H, m), 7.39-7.33 (1H, m), 7.27 (1H, t, J=8.1 Hz), 7.18 (2H, d, 10.4 Hz), 7.06-6.97 (2H, m), 2.50-2.43 (1H, m), 1.93-1.86 (4H, m), 1.49-1.38 (2H, m), 1.36-1.26 (3H, m), 1.24-1.18 (2H, m), 1.11-1.00 (2H, m), 0.91 (3H, t, J=7.1 Hz)

Example 3

Production of [3,5-difluoro-4-(2-fluoro-4-(trans-4-propylcyclohexyl)phenyl)phenyl]-[3-fluoro-4-(5,6,7-trifluoro-2-naphthyl)phenyloxy]difluoromethane

[Chem. 29]

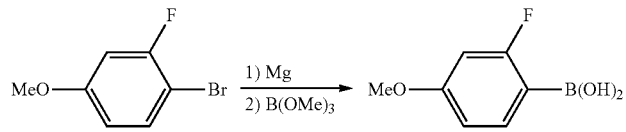

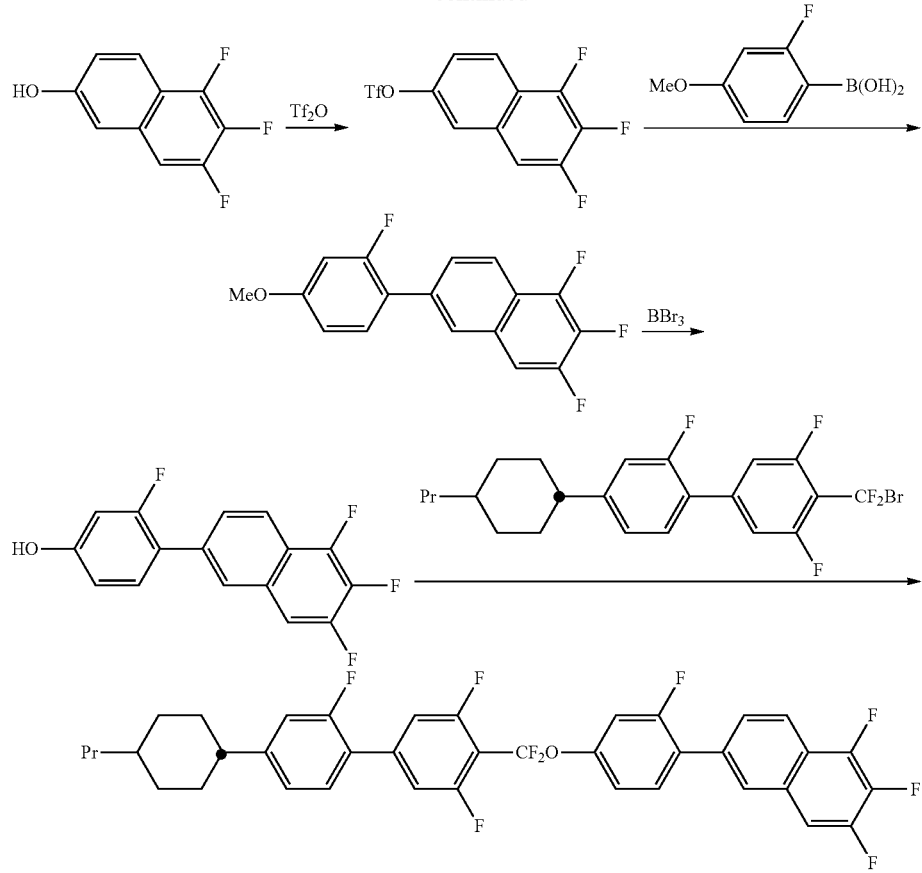

(3-1) In a nitrogen atmosphere, metal magnesium (3.9 g) was suspended in THF (5 mL), a solution prepared by dissolving 4-bromo-3-fluoroanisole (30 g) in THF (150 mL) was added at a rate at which the solution was gently refluxed, and stirring was performed at 40° C. for one hour. Subsequently, the reaction liquid was cooled to 5° C. After a solution prepared by dissolving trimethyl borate (19.8 g) in THF (60 mL) was added thereto, stirring was performed at room temperature for one hour. Toluene (150 mL) and 10% hydrochloric acid (100 mL) were added thereto and the mixture was separated. Toluene (100 mL) was added to the resulting aqueous layer and extraction was performed. The obtained organic layers were mixed and washed with a saturated saline solution (100 mL). Anhydrous sodium sulfate was added to perform drying, and the organic solvent was distilled off under reduced pressure. Thus, a crude 2-fluoro-4-methoxyphenylboric acid (26.3 g) was obtained.

(3-2) In a nitrogen atmosphere, 5,6,7-trifluoro-2-naphthol (30 g) and pyridine (15.6 g) were dissolved in dichloromethane (150 mL) and cooled to 5° C., and a solution prepared by dissolving trifluoromethanesulfonic acid anhydride (47.0 g) in dichloromethane (150 mL) was added thereto. After stirring was performed at room temperature for one hour, water (200 mL) was added and the mixture was separated. The resulting organic layer was washed with 10% hydrochloric acid (150 mL), an aqueous saturated sodium hydrogen carbonate solution (150 mL), and a saturated saline solution (150 mL). Anhydrous sodium sulfate was added to perform drying, and the organic solvent was distilled off under reduced pressure. Purification was performed by silica gel column chromatography to obtain 5,6,7-trifluoro-2-naphthyl trifluoromethanesulfonate (49.4 g).

(3-3) In a nitrogen atmosphere, the 5,6,7-trifluoro-2-naphthyl trifluoromethanesulfonate obtained in (3-2) (40.0 g), tetrakis(triphenylphosphine)palladium (0) (1.4 g), a 2 mol/L aqueous potassium carbonate solution (120 mL), and THF (200 mL) were mixed with each other and heated to 60° C. A solution prepared by dissolving 2-fluoro-4-methoxyphenylboric acid (24.7 g) obtained in (3-1) in THF (100 mL) was added thereto, and stirring was performed at 60° C. for six hours. The temperature was decreased to room temperature. Toluene (150 mL) was added thereto and the mixture was separated. The resulting organic layer was washed with water (100 mL) and a saturated saline solution (100 mL). Anhydrous sodium sulfate was added to perform drying, and the organic solvent was distilled off under reduced pressure. The resulting residue was purified by silica gel column chromatography to obtain a crude 2-(2-fluoro-4-methoxyphenyl)-5,6,7-trifluoronaphthalene (35.1 g).

(3-4) The crude 2-(2-fluoro-4-methoxyphenyl)-5,6,7-trifluoronaphthalene (35.1 g) obtained in (3-3) was dissolved in dichloromethane (350 mL) and cooled to 5° C., and boron tribromide (14.4 g) was added thereto. After stirring was performed at room temperature for three hours, the temperature was decreased to 5° C. Water (100 mL) was added thereto and the mixture was separated. The resulting organic layer was washed with a saturated saline solution (100 mL) twice. Anhydrous sodium sulfate was added to perform drying, and the organic solvent was distilled off under reduced pressure. The resulting residue was purified by alumina column chromatography and recrystallized using hexane to obtain 4-(5,6,7-trifluoro-2-naphthyl)-3-fluorophenol (25.3 g).

(3-5) The subsequent processes were performed by the same method as in Example 1 to obtain [3,5-difluoro-4-(2-fluoro-4-(trans-4-propylcyclohexyl)phenyl)phenyl]-[3-fluoro-4-(5,6,7-trifluoro-2-naphthyl)phenyloxy]difluoromethane (49.9 g).

MS m/z: 672 [M$^+$]

$^1$HNMR (CDCl$_3$, TMS internal standard) δ (ppm)=8.03 (1H, d, J=9.2 Hz), 7.67-7.66 (2H, m), 7.49-7.46 (1H, m), 7.38-7.33 (1H, m), 7.27 (1H, t, J=8.0 Hz), 7.19 (2H, d, 10.4 Hz), 7.06-6.97 (2H, m), 6.83-6.82 (2H, m), 2.52-2.45 (1H, m), 1.93-1.86 (4H, m), 1.49-1.38 (2H, m), 1.36-1.26 (3H, m), 1.24-1.18 (2H, m), 1.11-1.00 (2H, m), 0.91 (3H, t, J=7.1 Hz)

Example 4

Production of [4-(4-(5,6,7-trifluoro-2-naphthyl)-3-fluorophenyl)phenyloxy]-(2,6-difluoro-4-propylphenyl)difluoromethane

[Chem. 30]

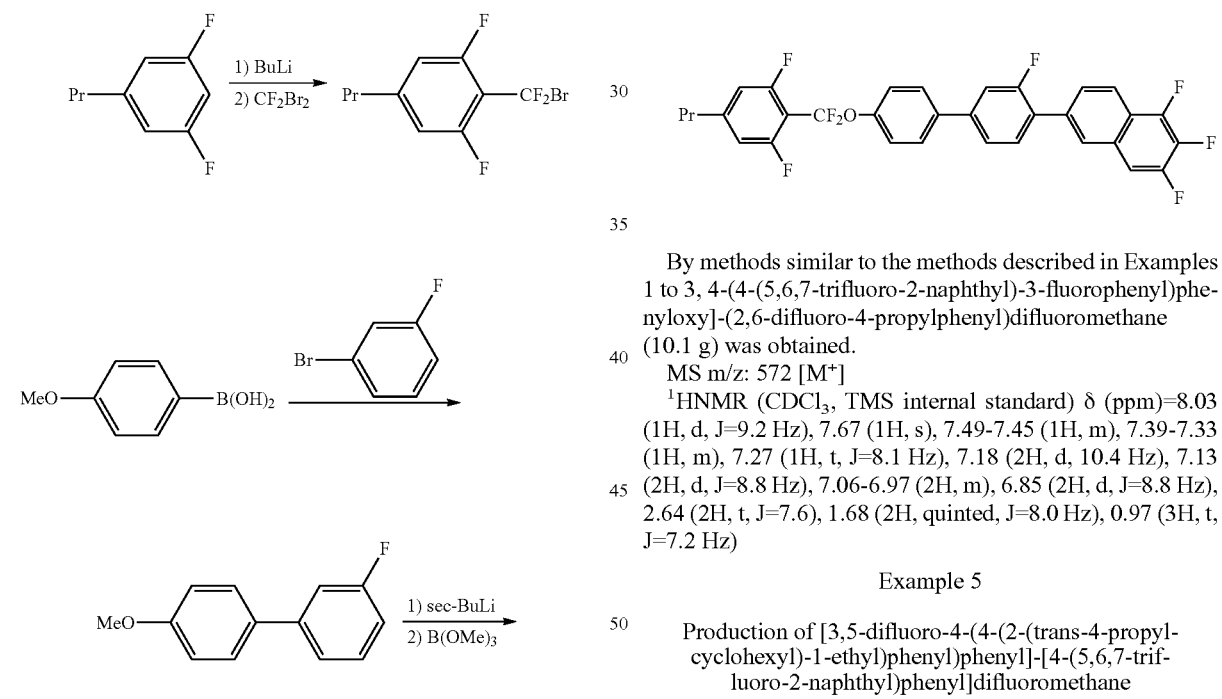

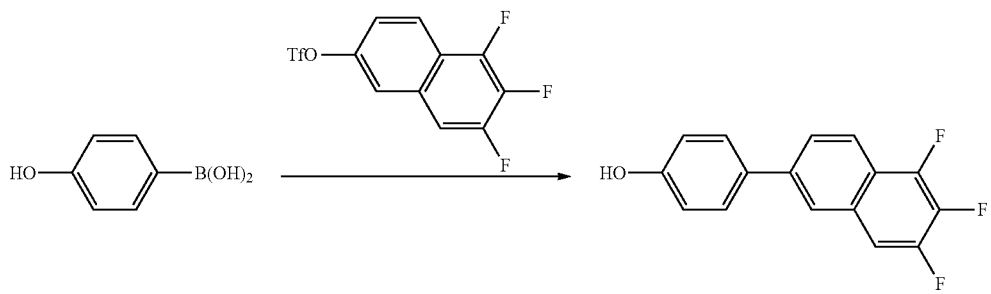

By methods similar to the methods described in Examples 1 to 3, 4-(4-(5,6,7-trifluoro-2-naphthyl)-3-fluorophenyl)phenyloxy]-(2,6-difluoro-4-propylphenyl)difluoromethane (10.1 g) was obtained.

MS m/z: 572 [M$^+$]

$^1$HNMR (CDCl$_3$, TMS internal standard) δ (ppm)=8.03 (1H, d, J=9.2 Hz), 7.67 (1H, s), 7.49-7.45 (1H, m), 7.39-7.33 (1H, m), 7.27 (1H, t, J=8.1 Hz), 7.18 (2H, d, 10.4 Hz), 7.13 (2H, d, J=8.8 Hz), 7.06-6.97 (2H, m), 6.85 (2H, d, J=8.8 Hz), 2.64 (2H, t, J=7.6), 1.68 (2H, quinted, J=8.0 Hz), 0.97 (3H, t, J=7.2 Hz)

Example 5

Production of [3,5-difluoro-4-(4-(2-(trans-4-propylcyclohexyl)-1-ethyl)phenyl)phenyl]-[4-(5,6,7-trifluoro-2-naphthyl)phenyl]difluoromethane

[Chem. 31]

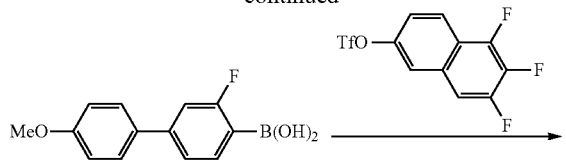

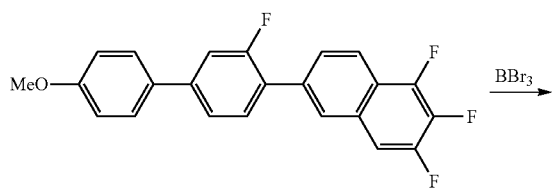

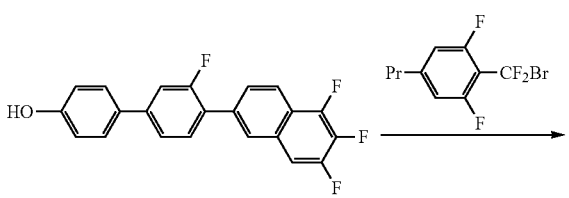

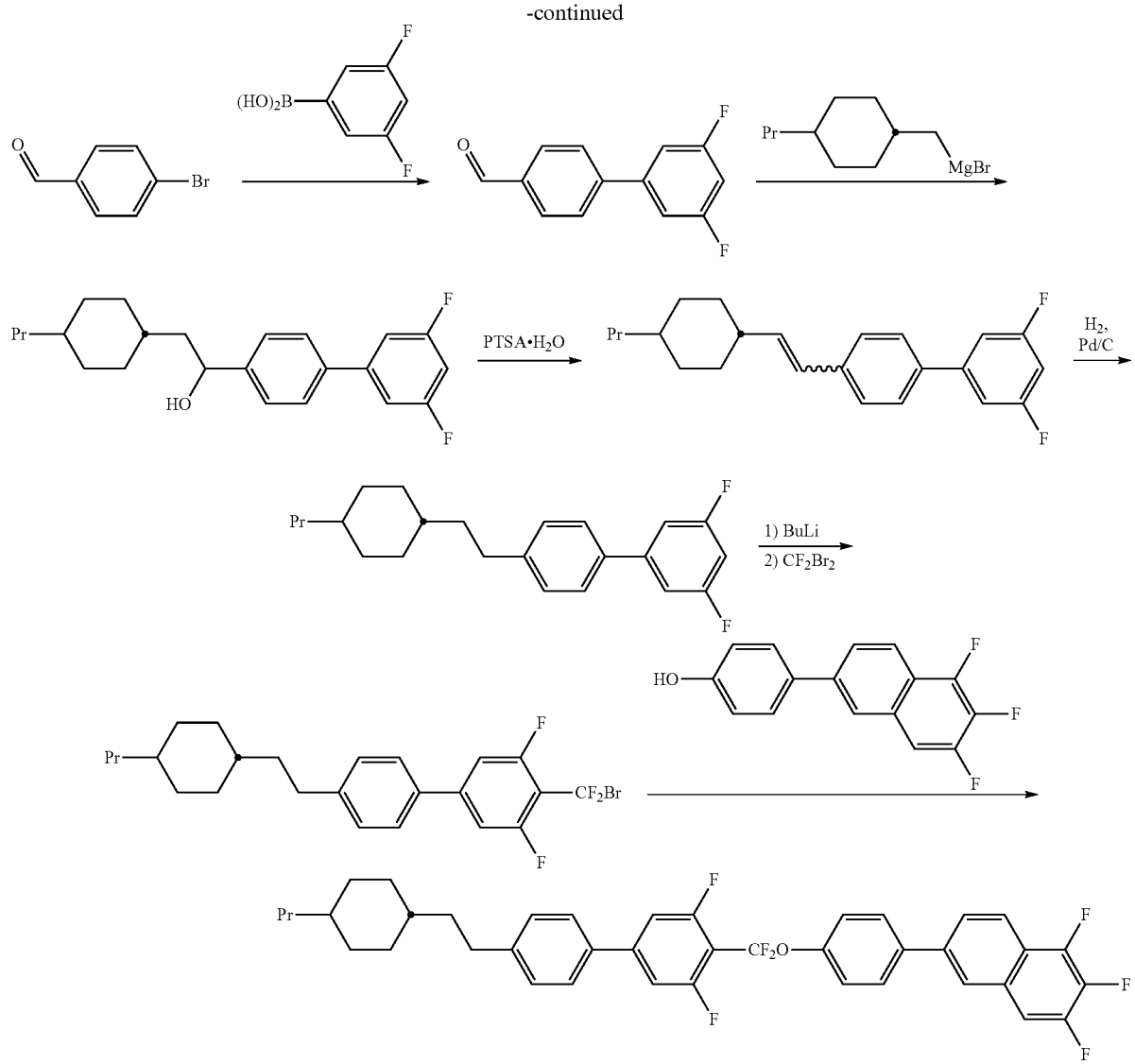

By methods similar to the methods described in Examples 1 to 3, [3,5-difluoro-4-(4-(2-(trans-4-propylcyclohexyl)-1-ethyl)phenyl)phenyl]-[4-(5,6,7-trifluoro-2-naphthyl)phenyl]difluoromethane (5.1 g) was obtained.

MS m/z: 664 [M+]

$^1$HNMR (CDCl$_3$, TMS internal standard) δ (ppm)=8.03 (1H, d, J=9.2 Hz), 7.67 (1H, s), 7.49-7.45 (3H, m), 7.42 (2H, d, J=7.9 Hz), 7.40-7.33 (3H, m), 7.27 (2H, d, J=8.0 Hz), 7.19 (2H, d, J=10.4 Hz), 2.38 (2H, t, J=7.0 Hz), 1.60-1.58 (2H, m), 1.40-1.17 (10H, m), 1.07-0.97 (4H, m), 0.90 (3H, t, J=7.2 Hz)

Example 6

Production of [3,5-difluoro-4-(2-fluoro-4-(4-propylphenyl)phenyl)phenyl]-(5,6,7-trifluoro-2-naphthyloxy)difluoromethane

[Chem. 32]

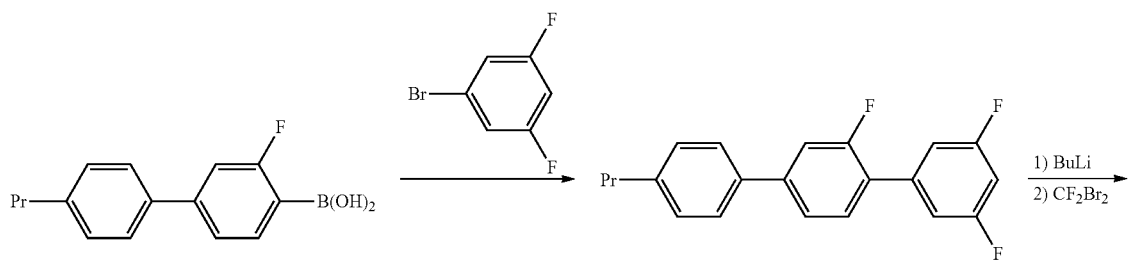

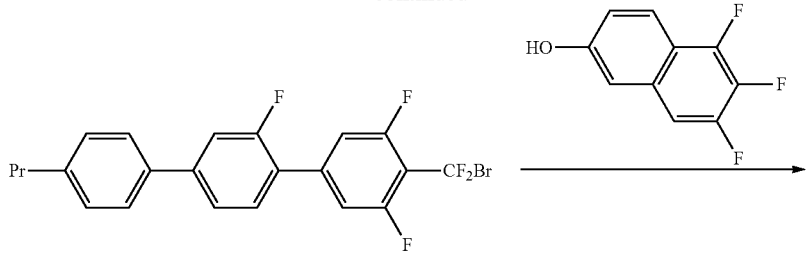

By a method similar to the method described in Example 2, 3,5-difluoro-4-(2-fluoro-4-(4-propylphenyl)phenyl]phenyl]-(5,6,7-trifluoro-2-naphthyloxy)difluoromethane (19.1 g) was obtained.

MS m/z: 572 [M$^+$]

Phase transition: Cr 99 N 217 Iso $^1$HNMR (CDCl$_3$, TMS internal standard) δ (ppm)=8.06 (1H, d, J=9.2 Hz), 7.71 (1H, s), 7.55-7.37 (7H, m), 7.27 (2H, d, J=10.1 Hz), 2.65 (2H, t, J=7.4 Hz), 1.69 (2H, sixtet, J=7.6 Hz), 0.98 (3H, t, J=7.3 Hz)

By methods similar to the methods described in Examples 1 to 3, [3,5-difluoro-4-(4-propylphenyl)phenyl]-(5,6,7-trifluoro-2-naphthyloxy)difluoromethane (24.1 g) was obtained.

MS m/z: 478 [M$^+$]

$^1$HNMR (CDCl$_3$, TMS internal standard) δ (ppm)=8.03 (1H, d, J=9.2 Hz), 7.67 (1H, s), 7.49-7.45 (3H, m), 7.38-7.33 (1H, m), 7.27 (2H, d, J=8.0 Hz), 7.19 (2H, d, 10.4 Hz), 2.63 (2H, d, 7.4 Hz), 1.67 (2H, quinted, J=7.6 Hz), 0.96 (3H, t, J=7.3 Hz)

Reference Example 1

Production of [3,5-difluoro-4-(4-propylphenyl)phenyl]-(5,6,7-trifluoro-2-naphthyloxy)difluoromethane Reference Example 2

Production of 5,6,7-trifluoro-2-[3-fluoro-4-(4-propylphenyl)phenyl]naphthalene

[Chem. 33]

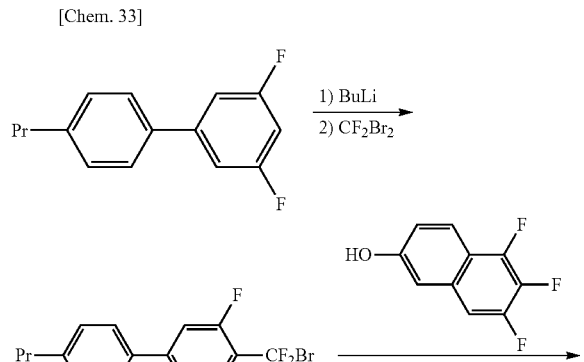

[Chem. 34]

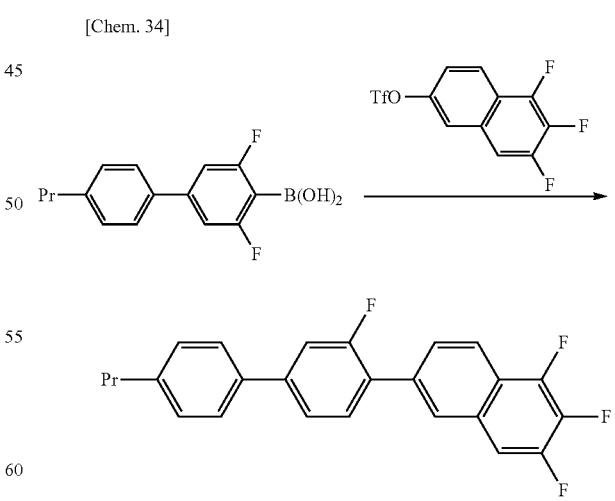

By methods similar to the methods described in Examples 1 to 3, 5,6,7-trifluoro-2-[3-fluoro-4-(4-propylphenyl)phenyl]naphthalene (50.1 g) was obtained.

MS m/z: 394 [M$^+$]

Example 7

Preparation of Liquid Crystal Composition—1

A host liquid crystal composition (H) having the following composition was prepared.

[Chem. 35]

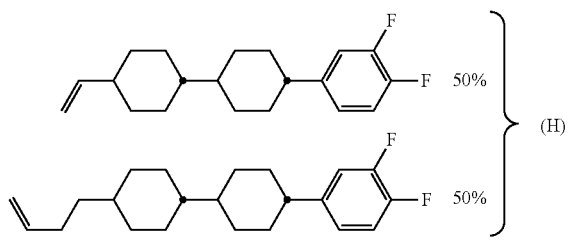

The physical properties of the composition (H) were as follows.
Nematic phase upper-limit temperature ($T_{ni}$): 117.2° C.
Dielectric anisotropy ($\Delta\in$): 4.38
Refractive index anisotropy ($\Delta n$): 0.0899
Viscosity ($\eta_{20}$): 20.3 mPa·s A liquid crystal composition (M-A) containing 80% of the host liquid crystal (H) and 20% of the [3,5-difluorotrans-4-(4-(trans-4-propylcyclohexyl)cyclohexyl)phenyl]-(5,6,7-trifluoro-2-naphthyloxy)difluoromethane obtained in Example 1 was prepared. The resulting composition had the following physical properties.
$T_{ni}$: 127.4° C.
$\Delta\in$: 8.44
$\Delta n$: 0.10232
$\eta_{20}$: 35.3 mPa·s It was found that the addition of the [3,5-difluoro-trans-4-(4-(trans-4-propylcyclohexyl)cyclohexyl)phenyl]-(5,6,7-trifluoro-2-naphthyloxy)difluoromethane increased $T_{ni}$ (extrapolated $T_{ni}$=168.2° C.) and increased $\Delta\in$ in a positive direction (extrapolated $\Delta\in$=24.7). Furthermore, the prepared liquid crystal composition (M-A) maintained a homogeneous nematic liquid crystal state at room temperature for one month or longer, which revealed that the liquid crystal composition (M-A) had good storage stability.

Example 8

Preparation of Liquid Crystal Composition—2

A liquid crystal composition (M-B) containing 80% of the host liquid crystal (H) and 20% of the [3,5-difluoro-4-(2-fluoro-4-(trans-4-propylcyclohexyl)phenyl)phenyl]-(5,6,7-trifluoro-2-naphthyloxy)difluoromethane obtained in Example 2 was prepared. The resulting composition had the following physical properties.
$T_{ni}$: 124.5° C.
$\Delta\in$: 10.88
$\Delta n$: 0.1135
$\eta_{20}$: 34.3 mPa·s It was found that the addition of the [3,5-difluoro-4-(2-fluoro-4-(trans-4-propylcyclohexyl)phenyl)phenyl]-(5,6,7-trifluoro-2-naphthyloxy)difluoromethane increased $T_{ni}$ (extrapolated $T_{ni}$=153.6° C.) and increased $\Delta\in$ in a positive direction (extrapolated $\Delta\in$=36.9). Furthermore, the prepared liquid crystal composition (M-B) maintained a homogeneous nematic liquid crystal state at room temperature for one month or longer, which revealed that the liquid crystal composition (M-B) had good storage stability.

Example 9

Preparation of Liquid Crystal Composition—3

A liquid crystal composition (M-C) containing 90% of the host liquid crystal (H) and 10% of the [3,5-difluoro-4-(2-fluoro-4-(trans-4-propylcyclohexyl)phenyl)phenyl]-[3-fluoro-4-(5,6,7-trifluoro-2-naphthyl)phenyloxy]difluoromethane obtained in Example 3 was prepared. The resulting composition had the following physical properties.
$T_{ni}$: 128.8° C.
$\Delta\in$: 8.30
$\Delta n$: 0.1106
$\eta_{20}$: 31.8 mPa·s It was found that the addition of the [3,5-difluoro-4-(2-fluoro-4-(trans-4-propylcyclohexyl)phenyl)phenyl]-[3-fluoro-4-(5,6,7-trifluoro-2-naphthyl)phenyloxy]difluoromethane considerably increased $T_{ni}$ (extrapolated $T_{ni}$=233.4° C.) and increased $\Delta\in$ in a positive direction (extrapolated $\Delta\in$=43.6). Furthermore, the prepared liquid crystal composition (M-C) maintained a homogeneous nematic liquid crystal state at room temperature for one month or longer, which revealed that the liquid crystal composition (M-C) had good storage stability.

Example 10

Preparation of Liquid Crystal Composition—4

A liquid crystal composition (M-D) containing 80% of the host liquid crystal (H) and 20% of the [4-(4-(5,6,7-trifluoro-2-naphthyl)-3-fluorophenyl)phenyloxy]-(2,6-difluoro-4-propylphenyl)difluoromethane obtained in Example 4 was prepared. The resulting composition had the following physical properties.
$T_{ni}$: 117.7° C.
$\Delta\in$: 9.77
$\Delta n$: 0.1481
$\eta_{20}$: 28.3 mPa·s It was found that the addition of the [4-(4-(5,6,7-trifluoro-2-naphthyl)-3-fluorophenyl)phenyloxy]-(2,6-difluoro-4-propylphenyl)difluoromethane relatively considerably increased $T_{ni}$ (extrapolated $T_{ni}$=119.7° C.) and increased $\Delta\in$ in a positive direction (extrapolated $\Delta\in$=31.2). Furthermore, the prepared liquid crystal composition (M-D) maintained a homogeneous nematic liquid crystal state at room temperature for one month or longer, which revealed that the liquid crystal composition (M-D) had good storage stability.

Example 11

Preparation of Liquid Crystal Composition—5

A liquid crystal composition (M-E) containing 95% of the host liquid crystal (H) and 5% of the [3,5-difluoro-4-(4-(2-(trans-4-propylcyclohexyl)-1-ethyl)phenyl)phenyl]-[4-(5,6,7-trifluoro-2-naphthyl)phenyl]difluoromethane obtained in Example 5 was prepared. The resulting composition had the following physical properties.
$T_{ni}$: 126.1° C.
$\Delta\in$: 5.63
$\Delta n$: 0.1017
$\eta_{20}$: 30.8 mPa·s It was found that the addition of the [3,5-difluoro-4-(4-(2-(trans-4-propylcyclohexyl)-1-ethyl)phenyl)phenyl]-[4-(5,6,7-trifluoro-2-naphthyl)phenyl]difluoromethane extremely increased $T_{ni}$ (extrapolated $T_{ni}$=294.5° C.) and increased $\Delta\in$ in a positive direction (extrapolated $\Delta\in$=29.3). Furthermore, the prepared liquid crystal composition (M-E) maintained a homogeneous nematic liquid crystal state at room temperature for one month or longer, which revealed that the liquid crystal composition (M-E) had good storage stability.

Example 12

Preparation of Liquid Crystal Composition—6

A liquid crystal composition (M-F) containing 90% of the host liquid crystal (H) and 10% of the [3,5-difluoro-4-(2-fluoro-4-(4-propylphenyl)phenyl)phenyl]-(5,6,7-trifluoro-2-naphthyloxy)difluoromethane obtained in Example 6 was prepared. The resulting composition had the following physical properties.

$T_{ni}$: 123.3° C.
$\Delta\in$: 7.51
$\Delta$n: 0.1060
$\eta_{20}$: 26.2 mPa·s

It was found that the addition of the [3,5-difluoro-4-(2-fluoro-4-(4-propylphenyl)phenyl)phenyl]-(5,6,7-trifluoro-2-naphthyloxy)difluoromethane considerably increased $T_{ni}$ (extrapolated $T_{ni}$=178.2° C.) and increased $\Delta\in$ in a positive direction (extrapolated $\Delta\in$=32.3). Furthermore, the prepared liquid crystal composition (M-F) maintained a homogeneous nematic liquid crystal state at room temperature for one month or longer, which revealed that the liquid crystal composition (M-F) had good storage stability.

Comparative Example 1

Preparation of Liquid Crystal Composition—7

A liquid crystal composition (M-G) containing 80% of the host liquid crystal (H) and 20% of the [3,5-difluoro-4-(4-propylphenyl)phenyl]-(5,6,7-trifluoro-2-naphthyloxy)difluoromethane obtained in Reference Example 1 was prepared. The resulting composition had the following physical properties.

$T_{ni}$: 106.9° C.
$\Delta\in$: 9.79
$\Delta$n: 0.1112
$\eta_{20}$: 26.9 mPa·s

It was found that the addition of the [3,5-difluoro-4-(4-propylphenyl)phenyl]-(5,6,7-trifluoro-2-naphthyloxy)difluoromethane decreased $T_{ni}$ (extrapolated $T_{ni}$=65.8° C.) and increased $\Delta\in$ in a positive direction (extrapolated $\Delta\in$=31.4). The prepared liquid crystal composition (M-G) maintained a homogeneous nematic liquid crystal state at room temperature for one month or longer, which revealed that the liquid crystal composition (M-G) had good storage stability.

Comparative Example 2

Preparation of Liquid Crystal Composition—8

A liquid crystal composition (M-H) containing 90% of the host liquid crystal (H) and 10% of the 5,6,7-trifluoro-2-[3-fluoro-4-(4-propylphenyl)phenyl]naphthalene was prepared. The resulting composition had the following physical properties.

$T_{ni}$: 119.6° C.
$\Delta\in$: 6.15
$\Delta$n: 0.1137
$\eta_{20}$: 23.8 mPa·s

It was found that the addition of the 5,6,7-trifluoro-2-[3-fluoro-4-(4-propylphenyl)phenyl]naphthalene increased $T_{n\text{-}i}$ to some extent (extrapolated $T_{ni}$=140.8° C.) and increased $\Delta\in$ in a positive direction (extrapolated $\Delta\in$=22.1). When the prepared liquid crystal composition (M-H) was stored at room temperature for two weeks, crystals were precipitated.

As a result of the comparison between Example 7 and Comparative Example 1, it was found that the compound of the present invention considerably increased $T_{ni}$ and $\Delta\in$ while the compound of the present invention had better storage stability than the reference compound. As a result of the comparison between Example 7 and Comparative Example 2, it was also found that the compound of the present invention considerably improved the storage stability and $\Delta\in$ while the compound of the present invention maintained high Tni.

The invention claimed is:
1. A compound represented by general formula (1),

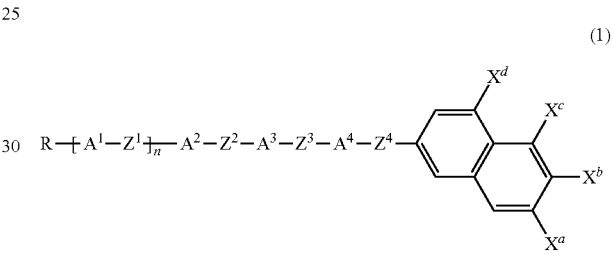

(in the formula, R represents an alkyl group having 1 to 15 carbon atoms or an alkenyl group having 2 to 15 carbon atoms; one —CH$_2$— or two or more non-adjacent —CH$_2$— in the groups may be each independently substituted with —O—, —S—, —COO—, —OCO—, or —CO—;

$A^1$ to $A^4$ are each independently selected from the group consisting of
(a) a 1,4-cyclohexylene group (one —CH$_2$— in this group may be substituted with —S— and two or more non-adjacent —CH$_2$— in this group may be each independently substituted with —O— or —S—) and
(b) a 1,4-phenylene group (one —CH= or two or more non-adjacent —CH= in this group may be substituted with —N=, and a hydrogen atom in this group may be substituted with a fluorine atom or a chlorine atom);

$Z^1$ to $Z^4$ each independently represent —CF$_2$O—, —OCF$_2$—, —CH$_2$CH$_2$—, —CF$_2$CF$_2$—, —CH=CH—, —CF=CF—, —C≡C—, or a single bond, and at least one of $Z^1$ to $Z^4$ present in the compound represents —CF$_2$O— or —OCF$_2$—;

$X^a$ to $X^d$ each independently represent a hydrogen atom, a fluorine atom, or a chlorine atom; and n represents 0 or 1).

2. The compound according to claim 1, wherein in the general formula (1), $Z^1$ and $Z^2$ present in the compound represent a single bond.

3. The compound according to claim 1, wherein in the general formula (1), $X^d$ represents a hydrogen atom.

4. The compound according to claim 1, wherein in the general formula (1), $A^1$ to $A^4$ present in the compound each independently represent one of groups below,

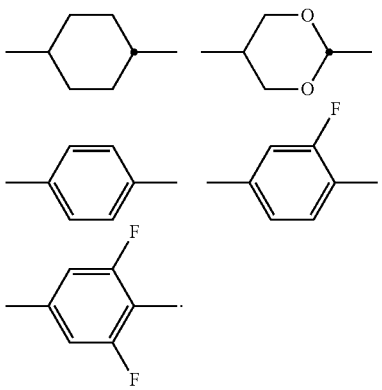

5. The compound according to claim 1, wherein in the general formula (1), $X^a$ to $X^c$ represent a fluorine atom.

6. The compound according to claim 1, wherein in the general formula (1), n represents 0.

7. The compound according to claim 1, wherein in the general formula (1), n represents 1.

8. The compound according to claim 1, wherein in the general formula (1), $Z^3$ represents —CF$_2$O— and $Z^4$ represents a single bond.

9. The compound according to claim 1, wherein in the general formula (1), $Z^3$ represents a single bond and $Z^4$ represents —CF$_2$O—.

10. A liquid crystal composition comprising at least one of the compound according to claim 1.

11. A liquid crystal display device using the liquid crystal composition according to claim 10.

* * * * *